(12) United States Patent
Brat et al.

(10) Patent No.: US 10,006,020 B2
(45) Date of Patent: Jun. 26, 2018

(54) PROKARYOTIC XYLOSE ISOMERASE FOR THE CONSTRUCTION OF XYLOSE-FERMENTING YEASTS

(71) Applicant: LESAFFRE ET COMPAGNIE, Paris (FR)

(72) Inventors: Dawid Brat, Frankfurt (DE); Eckhard Boles, Darmstadt (DE); Marco Keller, Bornheim (DE); Beate Rother, Einbeck (DE)

(73) Assignee: LESAFFRE ET COMPAGNIE, Paris (FR)

( * ) Notice: Subject to any disclaimer, the term of this patent is extended or adjusted under 35 U.S.C. 154(b) by 0 days. days.

(21) Appl. No.: 14/572,137

(22) Filed: Dec. 16, 2014

(65) Prior Publication Data
US 2015/0099276 A1     Apr. 9, 2015

Related U.S. Application Data

(63) Continuation of application No. 13/001,326, filed as application No. PCT/EP2009/004762 on Jul. 1, 2009, now Pat. No. 8,986,948.

(30) Foreign Application Priority Data

Jul. 2, 2008 (DE) .................. 10 2008 031 350

(51) Int. Cl.
| | |
|---|---|
| *C12P 7/56* | (2006.01) |
| *C12P 7/54* | (2006.01) |
| *C12P 7/46* | (2006.01) |
| *C12P 7/02* | (2006.01) |
| *C12P 7/18* | (2006.01) |
| *C12P 7/20* | (2006.01) |
| *C12P 7/16* | (2006.01) |
| *C12P 7/06* | (2006.01) |
| *C12P 5/00* | (2006.01) |
| *C12P 5/02* | (2006.01) |
| *C12P 1/02* | (2006.01) |
| *C12N 9/90* | (2006.01) |
| *C12N 1/00* | (2006.01) |
| *C12P 21/00* | (2006.01) |
| *C12P 19/34* | (2006.01) |
| *C12N 15/00* | (2006.01) |
| *C07H 21/04* | (2006.01) |
| *C07K 1/00* | (2006.01) |
| *C12N 9/92* | (2006.01) |
| *C12P 7/10* | (2006.01) |

(Continued)

(52) U.S. Cl.
CPC .................. *C12N 9/92* (2013.01); *C12P 7/06* (2013.01); *C12P 7/065* (2013.01); *C12P 7/10* (2013.01); *C12P 7/16* (2013.01); *C12P 19/02* (2013.01); *C12P 19/24* (2013.01); *C12Y 503/01005* (2013.01); *Y02E 50/10* (2013.01); *Y02E 50/16* (2013.01); *Y02E 50/17* (2013.01)

(58) Field of Classification Search
CPC .... C12N 9/92; C12P 7/06; C12P 7/065; C12P 7/10; C12P 7/16; C12P 19/02; C12P 19/24; C12Y 503/01005; Y02E 50/16; Y02E 50/17; Y02E 50/101
USPC ....... 435/139, 140, 145, 155, 158, 159, 160, 435/161, 166, 171, 233, 254.11, 254.21, 435/69.1, 91.1, 320.1; 536/23.1, 23.2; 530/350
See application file for complete search history.

(56) References Cited

U.S. PATENT DOCUMENTS

| | | | |
|---|---|---|---|
| 6,333,181 B1 * | 12/2001 | Ingram ................ | C12N 13/00 435/163 |
| 6,475,768 B1 | 11/2002 | Otero et al. | |

(Continued)

FOREIGN PATENT DOCUMENTS

| | | |
|---|---|---|
| WO | WO 03/062430 | 7/2003 |
| WO | WO 2007/089677 | 8/2007 |
| WO | WO 2008/141174 | 11/2008 |

OTHER PUBLICATIONS

Dmytruk et al., Overexpression of bacterial xylose isomerase and yeast host xylulokinase improves xylose alcoholic fermentation in the thermotolerant yeast Hansenula polymorpha. FEMS Yeast Res., 2008, vol. 8: 165-173.*

(Continued)

*Primary Examiner* — Ganapathirama Raghu
(74) *Attorney, Agent, or Firm* — Saliwanchik, Lloyd & Eisenschenk

(57) ABSTRACT

The present invention relates to the use of nucleic acid molecules coding for a bacterial xylose isomerase (XI), preferably coming from *Clostridium phytofermentans*, for reaction/metabolization, particularly fermentation, of recombinant microorganisms of biomaterial containing xylose, and particularly for the production of bioalcohols, particularly bioethanol, by means of xylose fermenting yeasts. The present invention further relates to cells, particularly eukaryotic cells, which are transformed utilizing a nucleic acid expression construct which codes for a xylose isomerase, wherein the expression of the nucleic acid expression construct imparts to the cells the capability to directly isomerize xylose into xylulose. Said cells are preferably utilized for reaction/metabolization, particularly fermentation, of biomaterial containing xylose, and particularly for the production of bioalcohols, particularly bioethanol. The present invention also relates to methods for the production of bioethanol, and to methods for the production of further metabolization products, comprising the metabolization of media containing xylose.

20 Claims, 9 Drawing Sheets

(51) Int. Cl.
*C12P 19/24* (2006.01)
*C12P 19/02* (2006.01)

(56) References Cited

U.S. PATENT DOCUMENTS

| | | | |
|---|---|---|---|
| 8,129,171 B2* | 3/2012 | Boles | C12N 1/18 435/254.21 |
| 8,435,770 B2* | 5/2013 | Hogsett | C12N 9/0006 435/161 |

OTHER PUBLICATIONS

Brat et al., "Functional expression of a bacterial xylose isomerase in *Saccharomyces cerevisiae*", *Applied and Environmental Microbiology*, Apr. 2009, vol. 75, No. 8, pp. 2304-2311.

Broun et al., Catalytic plasticity of fatty acid modification enzymes underlying chemical diversity of plant lipids. Science, 1998, vol. 282: 1315-1317.

Jeffries et al., "Metabolic engineering for improved fermentation of pentoses by yeasts", *Applied Microbiology and Biotechnology*, Jan. 2004, vol. 63, No. 5, pp. 495-509.

Kuyper et al., "High-level functional expression of a fungal xylose isomerase: the key to efficient ethanolic fermentation of xylose by *Saccharomyces cerevisiae*?", *FEMS Yeast Research*, Oct. 2003, vol. 4, No. 1, pp. 69-78.

Kuyper et al., "Minimal metabolic engineering of *Saccharomyces cerevisiae* for efficient anaerobic xylose fermentation: a proof of principle", *FEMS Yeast Research*, Mar. 2004, vol. 4, No. 6, pp. 655-664.

Leschine et al. UniProtKB/TrEMBL database, sequence entry dated Feb. 5, 2008.

Seffernick et al., Melamine deaminase and Atrazine chlorohydrolase: 98 percent identical but functionally different. J. Bacteriol., 2001, vol. 183 (8): 2405-2410.

Van Maris et al., "Alcoholic fermentation of carbon sources in biomass hydrolysates by *Saccharomyces cerevisiae*: current status", *Antonie van Leeuwenhoek*, Oct. 2006, vol. 90, No. 4, pp. 391-418.

Van Maris et al., "Development of efficient xylose fermentation in *Saccharomyces cerevisiae*: xylose isomerase as a key component", *Advances in Biochemical Engineering, Biotechnology*, Jan. 2007, vol. 108, pp. 179-204.

Walfridsson et al., "Ethanolic fermentation of xylose with *Saccharomyces cerevisiae* harboring the *Thermus thermophilus* xylA gene, which expresses an active xylose (glucose) isomerase", *Applied and Environmental Microbiology*, Dec. 1996, vol. 62, No. 12, pp. 4648-4651.

Warnick et al. "*Clostridium phytofermentans* sp. nov., a cellulolytic mesophile from forest soil", *International Journal of Systematic and Evolutionary Microbiology*, Jul. 2002, vol. 52, No. 4, pp. 1155-1160.

Whisstock et al., Prediction of protein function from protein sequence. Q. Rev. Biophysics., 2003, vol. 36 (3): 307-340.

Wiedemann et al., "Codon-optimized bacterial genes improve L-Arabinose fermentation in recombinant *Saccharomyces cerevisiae*", *Applied and Environmental Microbiology*, Apr. 2008, vol. 74, No. 7, pp. 2043-2050.

Witkowski et al., Conversion of b-ketoacyl synthase to a Malonyl Decarboxylase by replacement of the active cysteine with glutamine. Biochemistry, 1999, vol. 38: 11643-11650.

* cited by examiner

SEQUENCE LISTING

```
<160> NUMBER OF SEQ ID NOS: 3

<210> SEQ ID NO 1
<211> LENGTH: 438
<212> TYPE: PRT
<213> ORGANISM: Clostridium phytofermentans

<400> SEQUENCE: 1

Met Lys Asn Tyr Phe Pro Asn Val Pro Glu Val Lys Tyr Glu Gly Pro
1               5                   10                  15

Asn Ser Thr Asn Pro Phe Ala Phe Lys Tyr Tyr Asp Ala Asn Lys Val
            20                  25                  30

Val Ala Gly Lys Thr Met Lys Glu His Cys Arg Phe Ala Leu Ser Trp
        35                  40                  45

Trp His Thr Leu Cys Ala Gly Gly Ala Asp Pro Phe Gly Val Thr Thr
    50                  55                  60

Met Asp Arg Thr Tyr Gly Asn Ile Thr Asp Pro Met Glu Leu Ala Lys
65                  70                  75                  80

Ala Lys Val Asp Ala Gly Phe Glu Leu Met Thr Lys Leu Gly Ile Glu
                85                  90                  95

Phe Phe Cys Phe His Asp Ala Asp Ile Ala Pro Glu Gly Asp Thr Phe
            100                 105                 110

Glu Glu Ser Lys Lys Asn Leu Phe Glu Ile Val Asp Tyr Ile Lys Glu
        115                 120                 125

Lys Met Asp Gln Thr Gly Ile Lys Leu Leu Trp Gly Thr Ala Asn Asn
    130                 135                 140

Phe Ser His Pro Arg Phe Met His Gly Ala Ser Thr Ser Cys Asn Ala
145                 150                 155                 160

Asp Val Phe Ala Tyr Ala Ala Ala Lys Ile Lys Asn Ala Leu Asp Ala
                165                 170                 175

Thr Ile Lys Leu Gly Gly Lys Gly Tyr Val Phe Trp Gly Gly Arg Glu
            180                 185                 190
```

Gly Tyr Glu Thr Leu Leu Asn Thr Asp Leu Gly Leu Glu Leu Asp Asn
            195                 200                 205

Met Ala Arg Leu Met Lys Met Ala Val Glu Tyr Gly Arg Ala Asn Gly
        210                 215                 220

Phe Asp Gly Asp Phe Tyr Ile Glu Pro Lys Pro Lys Glu Pro Thr Lys
225                 230                 235                 240

His Gln Tyr Asp Phe Asp Thr Ala Thr Val Leu Ala Phe Leu Arg Lys
                245                 250                 255

Tyr Gly Leu Glu Lys Asp Phe Lys Met Asn Ile Glu Ala Asn His Ala
            260                 265                 270

Thr Leu Ala Gly His Thr Phe Glu His Glu Leu Ala Met Ala Arg Val
        275                 280                 285

Asn Gly Ala Phe Gly Ser Val Asp Ala Asn Gln Gly Asp Pro Asn Leu
    290                 295                 300

Gly Trp Asp Thr Asp Gln Phe Pro Thr Asp Val His Ser Ala Thr Leu
305                 310                 315                 320

Ala Met Leu Glu Val Leu Lys Ala Gly Phe Thr Asn Gly Gly Leu
                325                 330                 335

Asn Phe Asp Ala Lys Val Arg Arg Gly Ser Phe Glu Phe Asp Asp Ile
            340                 345                 350

Ala Tyr Gly Tyr Ile Ala Gly Met Asp Thr Phe Ala Leu Gly Leu Ile
        355                 360                 365

Lys Ala Ala Glu Ile Ile Asp Asp Gly Arg Ile Ala Lys Phe Val Asp
    370                 375                 380

Asp Arg Tyr Ala Ser Tyr Lys Thr Gly Ile Gly Lys Ala Ile Val Asp
385                 390                 395                 400

Gly Thr Thr Ser Leu Glu Glu Leu Glu Gln Tyr Val Leu Thr His Ser
                405                 410                 415

Glu Pro Val Met Gln Ser Gly Arg Gln Glu Val Leu Gly Thr Ile Val
            420                 425                 430

Asn Asn Ile Leu Phe Arg
        435

<210> SEQ ID NO 2
<211> LENGTH: 1317
<212> TYPE: DNA
<213> ORGANISM: Clostridium phytofermentans

<400> SEQUENCE: 2
atgaaaaatt actttccaaa tgttccagaa gtaaaatacg aaggcccaaa ttcaacgaat      60
ccatttgctt ttaaatatta tgacgcaaat aaagttgtag cgggtaaaac aatgaaagag     120
cactgtcgtt ttgcattatc ttggtggcat actctttgtg caggtggtgc tgatccattc     180
ggtgtaacaa ctatggatag aacctacgga atatcacag atccaatgga acttgctaag     240
gcaaaagttg acgctggttt cgaattaatg actaaattag gaattgaatt cttctgtttc     300
catgacgcag atattgctcc agaaggtgat acttttgaag agtcaaagaa gaatcttttt     360
gaaatcgttg attacatcaa agagaagatg gatcagactg gtatcaagtt attatggggt     420
actgctaata actttagtca tccaagattt atgcatggtg cttccacatc ttgcaacgca     480
gacgtatttg catatgctgc tgctaagatt aagaatgcat tagatgcaac aattaaatta     540
ggcggtaaag gttatgtatt ctggggtggt cgtgaaggtt atgaaacact tcttaataca     600
gatttaggac ttgagcttga taatatggct agacttatga agatggctgt agagtatggc     660

| | |
|---|---|
| cgtgcaaatg gttttgatgg cgacttctat attgagccaa agccaaagga accaaccaag | 720 |
| catcaatatg attttgatac agcaaccgta cttgctttcc ttcgcaaata tggcttagaa | 780 |
| aaagatttca agatgaacat tgaagcaaac catgctactc ttgcaggtca tacctttgaa | 840 |
| catgaacttg caatggctag agttaatggt gcatttggtt ctgtagatgc aaaccagggt | 900 |
| gatccaaacc ttggatggga tacggatcaa ttcccaactg atgttcatag tgcaactctt | 960 |
| gcaatgcttg aagtacttaa ggctggtgga ttcactaacg gcggacttaa ctttgatgca | 1020 |
| aaggtaagac gtggttcctt cgaatttgat gatattgcat acggttatat tgcaggaatg | 1080 |
| gatactttg cacttggttt aattaaggct gctgagatta tcgacgatgg tagaatcgca | 1140 |
| aaatttgtag atgatcgtta tgcaagctat aaaacaggaa ttggtaaagc aattgtggat | 1200 |
| ggaactacat ctcttgaaga attagagcag tatgttttaa cacatagtga accagtaatg | 1260 |
| cagagtggtc gtcaggaagt tcttgaaaca atcgtaaata atattttatt tagataa | 1317 |

<210> SEQ ID NO 3
<211> LENGTH: 1317
<212> TYPE: DNA
<213> ORGANISM: Artificial Sequence
<220> FEATURE:
<223> OTHER INFORMATION: Nucleic acid sequence of the open reading frame
      (ORF) of the Xylose isomerase from C. phytofermentans in a
      Codon-optimized form

<400> SEQUENCE: 3

| | |
|---|---|
| atgaagaact acttcccaaa cgttccagaa gttaagtacg aaggtccaaa ctctaccaac | 60 |
| ccattcgctt tcaagtacta cgacgctaac aaggttgttg ctggtaagac catgaaggaa | 120 |
| cactgtagat tcgctttgtc ttggtggcac accttgtgtg ctggtggtgc tgacccattc | 180 |
| ggtgttacca ccatggacag aacctacggt aacattaccg acccaatgga attggctaag | 240 |
| gctaaggttg acgctggttt cgaattgatg accaagttgg gtattgaatt cttctgtttc | 300 |
| cacgacgctg acattgctcc agaaggtgac accttcgaag aatctaagaa gaacttgttc | 360 |
| gaaattgttg actacattaa ggaaaagatg gaccaaaccg gtattaagtt gttgtggggt | 420 |
| accgctaaca cttctctctca cccaagattc atgcacggtg cttctacctc ttgtaacgct | 480 |
| gacgttttcg cttacgctgc tgctaagatt aagaacgctt tggacgctac cattaagttg | 540 |
| ggtggtaagg gttacgtttt ctggggtggt agagaaggtt acgaaacctt gttgaacacc | 600 |
| gacttgggtt tggaattgga caacatggct agattgatga gatggctgt tgaataccggt | 660 |
| agagctaacg gttccgacgg tgacttctac attgaaccaa agccaaagga accaaccaag | 720 |
| caccaatacg acttcgacac cgctaccgtt ttggctttct tgagaaagta cggtttggaa | 780 |
| aaggacttca agatgaacat tgaagctaac cacgctacct tggctggtca caccttcgaa | 840 |
| cacgaattgg ctatggctag agttaacggt gctttcggtt ctgttgacgc taaccaaggt | 900 |
| gacccaaact ggggttggga caccgaccaa ttcccaaccg acgttcactc tgctaccttg | 960 |
| gctatgttgg aagttttgaa ggctggtggt tcaccaacg gtggtttgaa cttcgacgct | 1020 |
| aaggttagaa gaggttcttt cgaattcgac gacattgctt acggttacat tgctggtatg | 1080 |
| gacaccttcg ctttgggttt gattaaggct gctgaaatta tcgacgacgg tagaattgct | 1140 |
| aagttcgttg acgacagata cgcttcttac aagaccggta ttggtaaggc tattgttgac | 1200 |
| ggtaccacct ctcttgaaga attggaacaa tacgttttga cccactctga accagttatg | 1260 |
| caatctggta gacaagaagt tttggaaacc attgttaaca acattttgtt cagataa | 1317 |

US 10,006,020 B2

PROKARYOTIC XYLOSE ISOMERASE FOR THE CONSTRUCTION OF XYLOSE-FERMENTING YEASTS

CROSS REFERENCE TO A RELATED APPLICATION

This application is a Continuation Application of co-pending application Ser. No. 13/001,326, filed Mar. 15, 2011, now U.S. Pat. No. 8,986,948; which is a National Stage Application of International Application Number PCT/EP2009/004762, filed Jul. 1, 2009; which claims priority to German Patent Application No. 102008031350.5, filed Jul. 2, 2008; all of which are incorporated herein by reference in their entirety.

The Sequence Listing for this application is labeled "SeqList-asfiled.txt", which was created on Dec. 16, 2014, and is 8 KB. The entire content is incorporated herein by reference in its entirety.

FIELD OF THE INVENTION

The present invention relates to the use of nucleic acid molecules coding for a bacterial xylose isomerase (XI), preferably coming from *Clostridium phytofermentans*, for the conversion/metabolization, particularly fermentation, of biomaterial containing xylose with recombinant microorganisms, and particularly for the production of bioalcohols, particularly bioethanol, by means of xylose-fermenting yeasts. The present invention further relates to cells, particularly eukaryotic cells, which are transformed with a nucleic acid expression construct, which codes for a xylose isomerase (XI), wherein the expression of the nucleic acid expression construct imparts to the cells the capability to directly isomerize xylose into xylulose. Said cells are preferably utilized for the conversion/metabolization, particularly fermentation, of biomaterial containing xylose, and particularly for the production of bioalcohols, particularly bioethanol. The present invention also relates to methods for the production of bioethanol, and to methods for the production of further metabolization products, comprising the metabolization of media containing xylose.

BACKGROUND OF THE INVENTION

Thanks to its capacity to ferment sugar into ethanol and carbon dioxide, the brewer's, wine and baker's yeast *Saccharomyces cerevisiae* has already been used for centuries for the production of bread, wine and beer. Apart from the production of heterologous proteins, *S. cerevisiae* is used in biotechnology primarily in the production of ethanol for industrial purposes. In numerous industries, ethanol is used as a starting substrate for syntheses. Due to the ever decreasing oil reserves, increasing oil prices and continuously rising global need for petrol, ethanol is increasingly becoming more important as a fuel alternative.

To allow for an economic and efficient production of bioethanol, the use of lignocellulose-containing biomass, such as e.g. straw, waste material from the timber industry and agriculture and the organic proportion of everyday domestic refuse, is a prime option as a starting substrate. On the one hand, it is very cheap and, on the other hand, available in great quantities. The three major components of lignocellulose are lignin, cellulose and hemicellulose. Hemicellulose, after cellulose the second most occurring polymer, is a highly branched heteropolymer. It consists of pentoses (L-arabinose, D-xylose), uronic acids (4-0-methyl-D-glucuronic acid, D-galacturonic acid) and hexoses (D-mannose, D-galactose, L-rhamnose, D-glucose) (see FIG. 1). Even though hemicellulose can be more easily hydrolysed than cellulose, it features the pentoses L-arabinose and D-xylose, which normally cannot be converted by the yeast *S. cerevisiae*.

To be able to use pentoses for fermentations, they initially have to get into the cell via the plasma membrane. Although *S. cerevisiae* is not able to metabolize D-xylose, it can absorb it into the cell. However, *S. cerevisiae* does not possess any specific transporters. The transport takes place by means of the numerous hexose transporters. However, the affinity of the transporters for D-xylose is markedly lower than that for D-glucose (Kotter and Ciriacy, 1993). In yeasts, which can metabolize D-xylose, such as e.g. *P. stipitis*, *C. shehatae* or *P. tannophilus* (Du Preez et al., 1986), both unspecific low-affinity transporters, which transport D-glucose and specific high-affinity proton symporters only for D-xylose are present (Hahn-Hägerdahl et al., 2001).

Utilization of D-Xylose

Different bacteria, yeasts and fungi are able to metabolize xylose. In prokaryotes and eukaryotes, the metabolization of xylose mainly differs in the type of isomerization of xylose to xylulose. In prokaryotes, the conversion of xylose to xylulose takes place by means of the enzyme xylose isomerase (XI). In eukaryotes, xylose is mostly isomerized in two steps. Initially, xylose is reduced to xylitol by the NAD(P)H-dependent xylose reductase (XR) and further converted to xylulose by the NAD-dependent xylitol dehydrogenase (XDH). The subsequent phosphorylation reaction takes place in prokaryotes and eukaryotes by means of xylulokinase (XK).

The resulting intermediate xylulose-5-phosphate is an intermediate of the pentose phosphate pathway. The major part of the xylulose-5-phosphate enters the glycolysis in the form of fructose-6-phosphate and glyceraldehyde-3-phosphate and is therein further converted to pyruvate (Schaaff-Gerstenschläger and Miosga, 1997). Under fermentative conditions, the sugar is degraded further to ethanol by the pyruvate decarboxylase and the alcohol dehydrogenase. Under aerobic conditions, pyruvate can be oxidized to carbon dioxide in the citrate cycle by means of a series of reaction steps.

Utilization of D-Xylose in *S. cerevisiae*

In papers from Kotter and Ciriacy (1993), a recombinant *S. cerevisiae* strain, which was able to metabolize D-xylose was constructed for the first time. For this, the genes of the yeast *Pichia stipitis* coding for D-xylose reductase (XYL1) and xylitol dehydrogenase (XYL2) were heterologously expressed in the yeast *S. cerevisiae*. In later works, the endogenous xylulokinase (XKS1) was additionally overexpressed, which improved the D-xylose absorption into the cell as well as its conversion to ethanol (Ho et al., 1998; Eliasson et al., 2000). Despite the achieved improvements, the main by-product of the xylose conversion under oxygen-limiting conditions was xylitol. This is attributed to an imbalance in the redox balance, which is caused by the reaction initially taking place in the metabolic pathway preferably using NADPH, however, the second reaction solely producing NADH (Hahn-Hägerdal et al., 2001). Under aerobic conditions, the NADH formed by the xylitol dehydrogenase can be regenerated to NAD via the respiratory chain. Under anaerobic conditions, NAD cannot be regenerated and accumulation of NADH in the cell results. Without the cofactor NAD, the xylitol dehydrogenase xylitol cannot be converted further to xylulose.

Although the xylose reductase used in the mentioned paper originates from *P. stipitis*, which is able to also use NADH as a cofactor, besides NADPH (Metzger and Hollenberg, 1995), the disruption of the xylose fermentation results under strict anaerobic conditions.

A solution to the problem was to introduce a redox-neutral metabolic pathway into *S. cerevisiae*. In prokaryotes, the conversion of xylose to xylulose takes place by means of the enzyme xylose isomerase (XI). For a complete conversion of D-xylose, only the gene XI would have to be expressed additionally as an endogenous xylulokinase is present. Although a xylose isomerase could be detected in some fungi (Tomoyeda and Horitsu, 1964; Vongsuvanglert and Tani, 1988; Banerjee et al., 1994; Rawat et al., 1996), only the xylose degradation via the enzymes xylose reductase and xylitol dehydrogenase has been shown in eukaryotes. Many efforts to heterologously express a xylose isomerase from different organisms failed (Gárdonyi and Hahn-Hägerdal, 1993). In the majority of cases, the enzymes were not functional in yeast or they were not synthesized to proteins (Sarthy et al., 1987; Amore et al., 1989; Moes et al., 1996). With high activity, only the xylose isomerase could be expressed in yeast from the obligatory anaerobic fungus *Piromyces* sp. E2 (Kyper et al., 2003). When heterologously overexpressing this eukaryotic xylose isomerase (Harhangi et al., 2003), *S. cerevisiae* was able to grow on xylose and also metabolize it under anaerobic conditions (Kuyper et al., 2003). However, further tests showed that the enzyme is strongly inhibited by xylitol, a product of the xylose conversion. Xylitol is formed unspecifically in yeast from xylose by means of aldose reductases.

U.S. Pat. No. 6,475,768 describes the use of a prokaryotic thermophilic xylose isomerase from *Thermus thermophilus* and variants of this, respectively, for the metabolization of xylose by yeasts. The optimal temperature for this enzyme or the variants is at a temperature (>70° C.), which is markedly higher than the temperature at which yeast grows and metabolizes (28-35° C.); however, yeast is inactive or dies off at temperatures above 40° C. However, at temperatures of about 30° C., the xylose isomerase from *Thermus thermophilus* and also the variants are virtually inactive. Thus, this enzyme and its variants do not permit the yeast to effectively metabolize xylose.

Therefore, a need exists in the prior art for pentose isomerases, particularly xylose isomerases allowing for an improved and more efficient pentose conversion, particularly xylose conversion.

BRIEF SUMMARY

It is thus an object of the present invention to provide improved pentose isomerases, particularly xylose isomerases, for the use in the xylose conversion, which in particular can be used for industrial yeast strains.
Xylose Isomerase (XI) Constructs and their Use The object is achieved according to the invention by providing a nucleic acid molecule comprising a nucleic acid sequence, which codes for a prokaryotic xylose isomerase (XI), for
the transformation of a cell, preferably for the recombinant expression and production of the xylose isomerase,
the conversion of xylose to xylulose by the cell, and/or
the formation of secondary products from xylose by the cell.

In particular for the following uses:
the transformation of a cell, preferably for the recombinant expression/production of the prokaryotic xylose isomerase,
the conversion/metabolization, particularly fermentation, of biomaterial containing xylose,
the production of bio-based chemicals,
the production of biobutanol,
the production of bioethanol.

"Secondary products" should be understood to mean those compounds, which the cell further produces from the xylose converted to xylulose, such as, for example, bio-based chemicals and bioalcohols.

"Bio-based chemicals" should be understood to mean chemical compounds and substances, which are obtained from biological materials and raw materials (biomass), particularly by using microorganisms.

The bio-based chemicals can be compounds, which are selected from, but not limited to: lactic acid, acetic acid, succinic acid, malic acid, 1-butanol, isobutanol, 2-butanol, other alcohols, amino acids, 1,3-propanediol, ethylene, glycerine, a β-lactam antibiotic or a cephalosporin, alkanes, terpenes, isoprenoids or the precursor molecule amorphadiene of the antimalarial drug artemisinin.

The terms "conversion" and "metabolization" are used synonymously and mean the metabolism of a substance or the conversion of a substance in the course of the metabolism, here: the conversion of xylose, particularly the conversion of xylose to xylulose, by a cell, which was transformed with a nucleic acid according to the invention. A preferred conversion/metabolization is fermentation.

The nucleic acid molecules are recombinant nucleic acid molecules. Furthermore, nucleic acid molecules according to the invention comprise dsDNA, ssDNA, PNA, CNA, RNA or mRNA or combinations thereof.

DETAILED DESCRIPTION

The prokaryotic xylose isomerase (XI) according to the invention comes from *Clostridium phytofermentans*.

In this invention, it was achieved with a test system to express a highly functional prokaryotic xylose isomerase from *Clostridium phytofermentans* in the yeast *S. cerevisiae*. It could be shown that the xylose isomerase found allows recombinant yeasts to efficiently metabolize xylose.

The prokaryotic xylose isomerase (XI) according to the invention can be expressed in cells, particularly eukaryotic cells, in an active form. Additionally, the prokaryotic xylose isomerase (XI) according to the invention is less sensitive to an inhibition by xylitol than the eukaryotic xylose isomerase from an anaerobic fungus known from the prior art.

When the nucleic acid sequence coding for the prokaryotic xylose isomerase (XI) is expressed in a cell, the cell is imparted the capability to convert xylose to xylulose, which then may be metabolized further. Through this, the cell is able to grow on xylose as a carbon source.

The prokaryotic xylose isomerase (XI) according to the invention preferably comprises an amino acid sequence, which is at least 70% identical, preferably at least 80% identical, more preferably at least 90% identical, even more preferably at least 95% identical and yet more preferably 99% identical or identical to the amino acid sequence of SEQ ID NO: 1.

The nucleic acid sequence coding for a prokaryotic xylose isomerase (XI) preferably comprises a nucleic acid sequence, which is at least 70% identical, preferably at least 80% identical, more preferably at least 90% identical, even more preferably at least 95% identical and yet more preferably 99% identical or identical to the amino acid sequence of SEQ ID NO: 2.

The nucleic acid molecules according to the invention preferably comprise nucleic acid sequences, which are identical with the naturally occurring nucleic acid sequence or are codon-optimized for the use in a host cell.

Every amino acid is encrypted on a gene level by a codon. However, there are several different codons, which code for a single amino acid. Thus, the genetic code is degenerated. The preferred choice of a codon for a corresponding amino acid differs from organism to organism. Therefore, problems can arise in heterologously expressed genes if the host organism or the host cell has a very different codon usage. The gene can be expressed not at all or only slowly. Even in genes from different metabolic pathways within an organism, a different codon usage can be discovered. It is known that the glycolysis genes from *S. cerevisiae* are expressed strongly. They have a very restrictive codon usage. It can be assumed that by adapting the codon usage of the bacterial xylose isomerase gene to the codon usage of the glycolysis genes from *S. cerevisiae*, an improvement of the xylose conversion in yeast is achieved.

In a preferred embodiment, the nucleic acid sequence coding for a prokaryotic xylose isomerase (XI) comprises a nucleic acid sequence, which is codon-optimized for the use in a host cell.

The codon-optimization substantially preferably consists in an adaptation of the codon usage to the codon usage of the host organism/host cell, such as yeast. The codon usage of the bacterial xylose isomerase gene is preferably adapted to the codon usage of the glycolysis gene from *S. cerevisiae*. For further details, see also example 2 and table 1.

The nucleic acid sequence coding for a prokaryotic xylose isomerase (XI) preferably comprises a nucleic acid sequence, which is at least 70% identical, preferably at least 80% identical, more preferably at least 90% identical, even more preferably at least 95% identical and yet more preferably 99% identical or identical to the amino acid sequence of SEQ ID NO: 3.

The nucleic acid molecule used according to the invention is preferably a nucleic acid expression construct.

Nucleic acid expression constructs according to the invention are expression cassettes comprising a nucleic acid molecule according to the invention, or expression vectors comprising a nucleic acid molecule according to the invention or an expression cassette, for example.

A nucleic acid expression construct preferably comprises promoter and terminator sequences, the promoter being operatively linked with the nucleic acid sequence coding for a prokaryotic xylose isomerase (XI).

Preferred promoter sequences are selected from HXT7, truncated HXT7, PFK1, FBA1, PGK1, ADH1 and TDH3.

Preferred terminator sequences are selected from CYC1, FBA1, PGK1, PFK1, ADH1 and TDH3.

The nucleic acid expression construct may further comprise 5' and/or 3' recognition sequences and/or selection markers.

The selection marker is preferably selected from a LEU2 marker gene, a URA3 marker gene and a dominant antibiotic-resistance marker gene. A preferred dominant antibiotic-resistance marker gene is selected from genes, which impart resistances to geneticin, hygromycin and nourseothricin.

An expression vector can be selected from the group of pRS303X, p3RS305X, p3RS306X, pRS41 H, pRS41 K, pRS41 N, pRS42H, pRS42K, pRS42N or p423HXT7-6HIS, p424HXT7-6HIS, p425HXT7-6HIS, p426HXT7-6HIS.

The cell to be transformed is preferably a eukaryotic microorganism, preferably a yeast cell or a filamentous fungal cell.

The yeast cell is preferably a member of a genus selected from the group of *Saccharomyces, Kluyveromyces, Candida, Pichia, Schizosaccharomyces, Hansenula, Kloeckera, Schwanniomyces, Arxula* and *Yarrowia*.

The yeast cell is more preferably a member of a species selected from the group of *S. cerevisiae, S. bulderi, S. barnetti, S. exiguus, S. uvarum, S. diastaticus, K. lactis, K. marxianus* and *K. fragilis*.

The filamentous fungal cell is preferably a member of a genus selected from the group of *Aspergillus, Trichoderma, Humicola, Acremonium, Fusarium* and *Penicillium*.

Xylose-Fermenting Cells

The object is achieved according to the invention by providing cells, which are transformed with a nucleic acid expression construct coding for a prokaryotic xylose isomerase (XI).

A cell according to the invention is preferably a eukaryotic cell.

A cell according to the invention, particularly a eukaryotic cell, is transformed with a nucleic acid expression construct comprising:
(a) a nucleic acid sequence coding for a prokaryotic xylose isomerase (XI),
(b) a promoter operatively linked with the nucleic acid sequence, allowing for the expression of the prokaryotic xylose isomerase (XI) in the cell.

In this connection, the expression of the nucleic acid expression construct imparts to the cell the capability to directly isomerize xylose into xylulose.

As discussed above, the prokaryotic xylose isomerase (XI) according to the invention can be expressed in cells, particularly eukaryotic cells, in an active form such that the cells can thus directly isomerize xylose into xylulose (see also FIG. 2).

Additionally, the prokaryotic xylose isomerases (XI) according to the invention are less sensitive to an inhibition by xylitol than the eukaryotic xylose isomerases from an anaerobic fungus known from the prior art.

The inventors have introduced a redox-neutral metabolic pathway into *S. cerevisiae* in which the conversion of xylose to xylulose takes place by means of a xylose isomerase (XI) (FIG. 2).

When the nucleic acid sequence coding for the prokaryotic xylose isomerase (XI) is expressed in a cell, the cell is imparted the capability to convert xylose to xylulose, which then may be metabolized further. Through this, the cell is able to grow on xylose as a carbon source.

The prokaryotic xylose isomerase (XI) according to the invention preferably comes from *Clostridium phytofermentans*. The xylose isomerase (XI) according to the invention preferably comprises an amino acid sequence, which is at least 70% identical, preferably at least 80% identical, more preferably at least 90% identical, even more preferably at least 95% identical and yet more preferably 99% identical or identical to the amino acid sequence of SEQ ID NO: 1.

The promoter (b) is preferably selected from HXT7, truncated HXT7, PFK1, FBA1, PGK1, ADH1 and TDH3.

In a preferred embodiment, the nucleic acid expression construct with which a cell according to the invention is transformed is a nucleic acid molecule according to the invention, as defined herein and above.

The cell according to the invention is preferably a eukaryotic microorganism, preferably a yeast cell or a filamentous fungal cell.

A yeast cell according to the invention is preferably a member of a genus selected from the group of *Saccharomyces, Kluyveromyces, Candida, Pichia, Schizosaccharomyces, Hansenula, Kloeckera, Schwanniomyces, Arxula* and *Yarrowia*.

A yeast cell according to the invention is more preferably a member of a species selected from the group of *S. cerevisiae, S. bulderi, S. barnetti, S. exiguus, S. uvarum, S. diastaticus, K. lactis, K. marxianus* and *K. fragilis*.

A yeast cell according to the invention is more preferably the strain Ethanol Red™ or Lallemand1.

A filamentous fungal cell according to the invention is preferably a member of a genus selected from the group of *Aspergillus, Trichoderma, Humicola, Acremonium, Fusarium* and *Penicillium*.

The cell according to the invention is preferably a cell maintained in a cell culture or a cultured cell.

The cells according to the invention are transiently or stably transformed with the nucleic acid expression construct or the nucleic acid molecule, as defined herein.

In one embodiment, a cell according to the invention furthermore expresses one or more enzymes, which impart to the cell the capability to produce one or more further metabolization products.

In this connection, such a further metabolization product is preferably selected from, but not limited to, the group of bio-based chemicals, such as lactic acid, acetic acid, succinic acid, malic acid, 1-butanol, isobutanol, 2-butanol, other alcohols, amino acids, 1,3-propanediol, ethylene, glycerol, a β-lactam antibiotic or a cephalosporin, alkanes, terpenes, isoprenoids or the precursor molecule amorphadiene of the antimalarial drug artemisinin.

The object is achieved according to the invention by using the cells according to the invention for the conversion/metabolization, particularly fermentation, of biomaterial containing xylose and/or for the production of bioethanol.

The object is achieved according to the invention by using the corresponding cells according to the invention for the conversion/metabolization, particularly fermentation, of biomaterial containing xylose and/or for the production of a metabolization product.

In this connection, the metabolization product is preferably selected from the group of bio-based chemicals (but not limited to this group of bio-based chemicals), such as lactic acid, acetic acid, succinic acid, malic acid, 1-butanol, isobutanol, 2-butanol, other alcohols, amino acids, 1,3-propanediol, ethylene, glycerol, a β-lactam antibiotic or a cephalosporin, alkanes, terpenes, isoprenoids or the precursor molecule amorphadiene of the antimalarial drug artemisinin.

The object is achieved according to the invention by providing a method for the production of bioethanol.

The method according to the invention comprises the following steps:
(a) converting a medium containing a xylose source with a cell according to the invention, which converts xylose to ethanol,
(b) optionally obtaining the bioethanol.

The bioethanol is obtained by isolation, for example.

The medium may also contain another additional carbon source, particularly glucose.

The production of bioethanol preferably takes place at a rate of at least 0.03 g of ethanol per g of yeast dry weight and hour.

The ethanol yield is preferably at least 0.3 g of ethanol per g of xylose.

The object is achieved according to the invention by providing a method for the production of a metabolization product.

In this connection, such a further metabolization product is preferably selected from, but not limited to, the group of bio-based chemicals, such as lactic acid, acetic acid, succinic acid, malic acid, 1-butanol, isobutanol, 2-butanol, other alcohols, amino acids, 1,3-propanediol, ethylene, glycerol, a β-lactam antibiotic or a cephalosporin, alkanes, terpenes, isoprenoids or the precursor molecule amorphadiene of the antimalarial drug artemisinin.

The method according to the invention comprises the following steps:
(a) converting/metabolizing, particularly fermenting, a medium containing a xylose source with a corresponding cell according to the invention, which converts xylose to produce the metabolization product,
(b) optionally obtaining the metabolization product.

The metabolization product is obtained by isolation, for example.

The medium may also contain another additional carbon source, particularly glucose.

The inventors have succeeded to introduce a redox-neutral metabolic pathway into *S. cerevisiae* in which the conversion of xylose to xylulose takes place by means of a xylose isomerase (XI) (FIG. 2).

In this invention, it was achieved with a test system to express a highly functional prokaryotic xylose isomerase from *Clostridium phytofermentans* in the yeast *S. cerevisiae*. It could be shown that the xylose isomerase found allows recombinant yeasts to efficiently metabolize xylose.

Furthermore, a plurality of experimental obstacles and difficulties had to be overcome in finding a functional xylose isomerase:

5 genes had to be overexpressed for the construction of the test strain MKY09.

The choice of the xylose isomerases to be tested was not trivial.

All the bacterial xylose isomerases hitherto tested showed no to very low activity in yeast.

High expenditure in the cultivation of the organisms to be tested, which were needed for the screen.

The xylose isomerase according to the invention is the first described highly active prokaryotic xylose isomerase in yeast.

The xylose isomerase according to the invention is the first xylose isomerase of cluster II (of three clusters) of xylose isomerases (see FIG. 3), which could be expressed functionally in yeasts.

The xylose isomerase according to the invention is only slightly inhibited by xylitol.

Several reports about the difficulties with regard to the functional expression of xylose isomerases in yeast exist (Gárdonyi and Hahn-Hägerdahl, 2003; as well as reference cited therein).

The inventors have succeeded for the first time to express a prokaryotic xylose isomerase in functional form in yeasts such that they are enabled to metabolize xylose under physiological conditions and in significant quantities and to convert it to products (e.g. ethanol). As described in the prior art, this is not trivial. Numerous attempts were made and all of them were so far unsuccessful (see Sarthy et al., 1987; Amore et al., 1989; Moes et al., 1996, U.S. Pat. No. 6,475,768). The inventors have now succeeded to demonstrate that especially the *C. phytofermentans* xylose isomerase, in contrast to all the other, hitherto known prokaryotic enzymes, enable the yeast to metabolize xylose under physiological conditions and in significant quantities and to make products out of it.

Examples of lignocellulosic hydrolysates having a significant proportion of xylan (Hayn et al., 1993):
Grass: 16%
Wheat bran: 19%
Corn waste: 19%

BRIEF DESCRIPTION OF THE SEQUENCES

The present invention is clarified further in the following figures, sequences and examples, however, without being limited to these. The cited references are fully incorporated by reference herein. The sequences and figures show:

SEQ ID NO: 1 the protein sequence of the xylose isomerase ORF (open reading frame) of *C. phytofermentans*, (see also GenBank Accession Nos. ABX41597 and CP000885 (from 19 Nov. 2007)), SEQ ID NO: 2 the nucleic acid sequence of the open reading frame (ORF) of the xylose isomerase from *C. phytofermentans*, (see also GenBank Accession No. CP000885 (from 19 Nov. 2007)), SEQ ID NO: 3 the nucleic acid sequence of the open reading frame (ORF) of the xylose isomerase from *C. phytofermentans* in a codon-optimized form.

Figure 1:
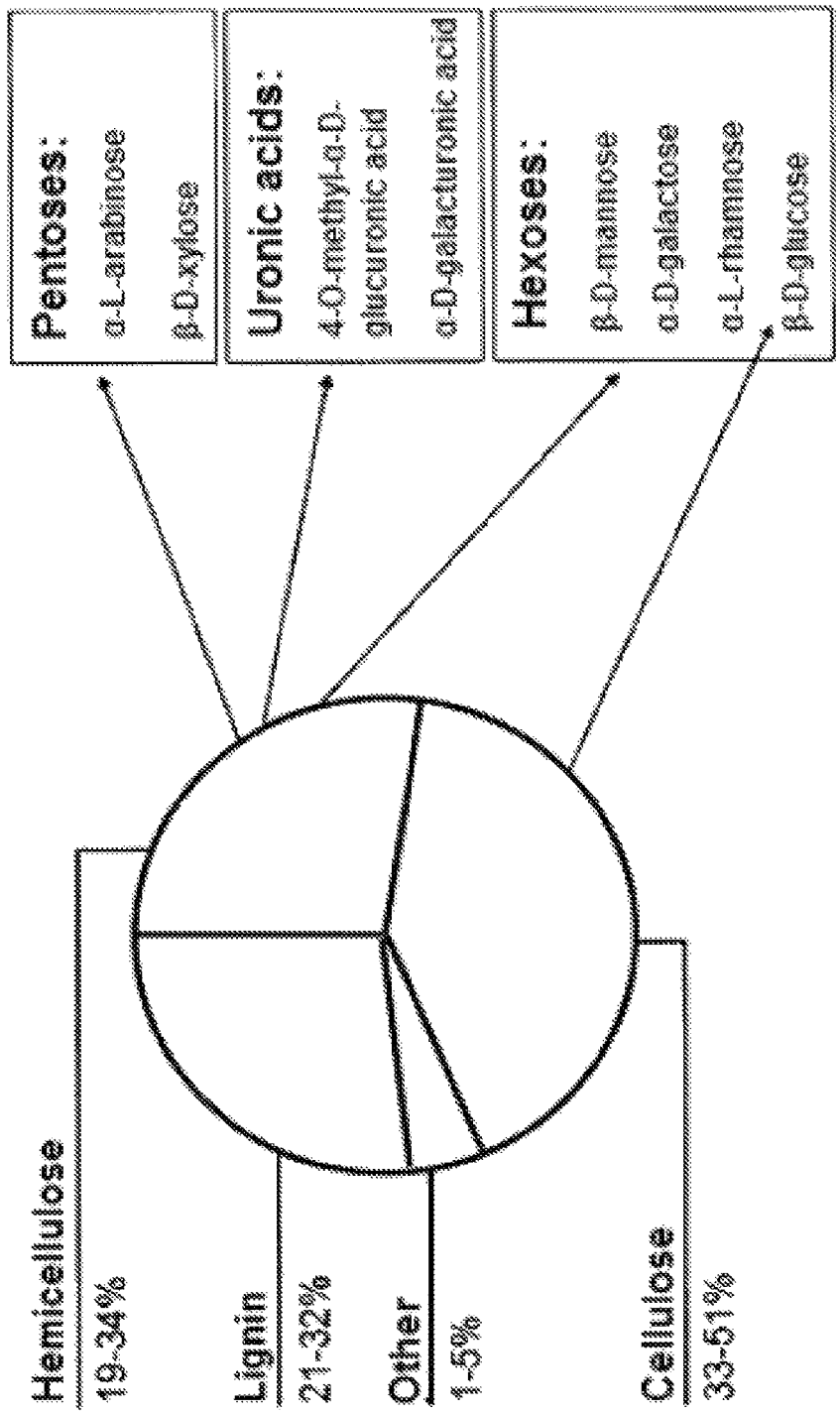
FIG. 1. Composition of biomass. Biomass consists of cellulose, hemicellulose and lignin. The second most occurring hemicellulose is a highly branched polymer consisting of pentoses, uronic acids and hexoses. To a large proportion, the hemicellulose consists of the pentoses xylose and arabinose.
Figure 2:
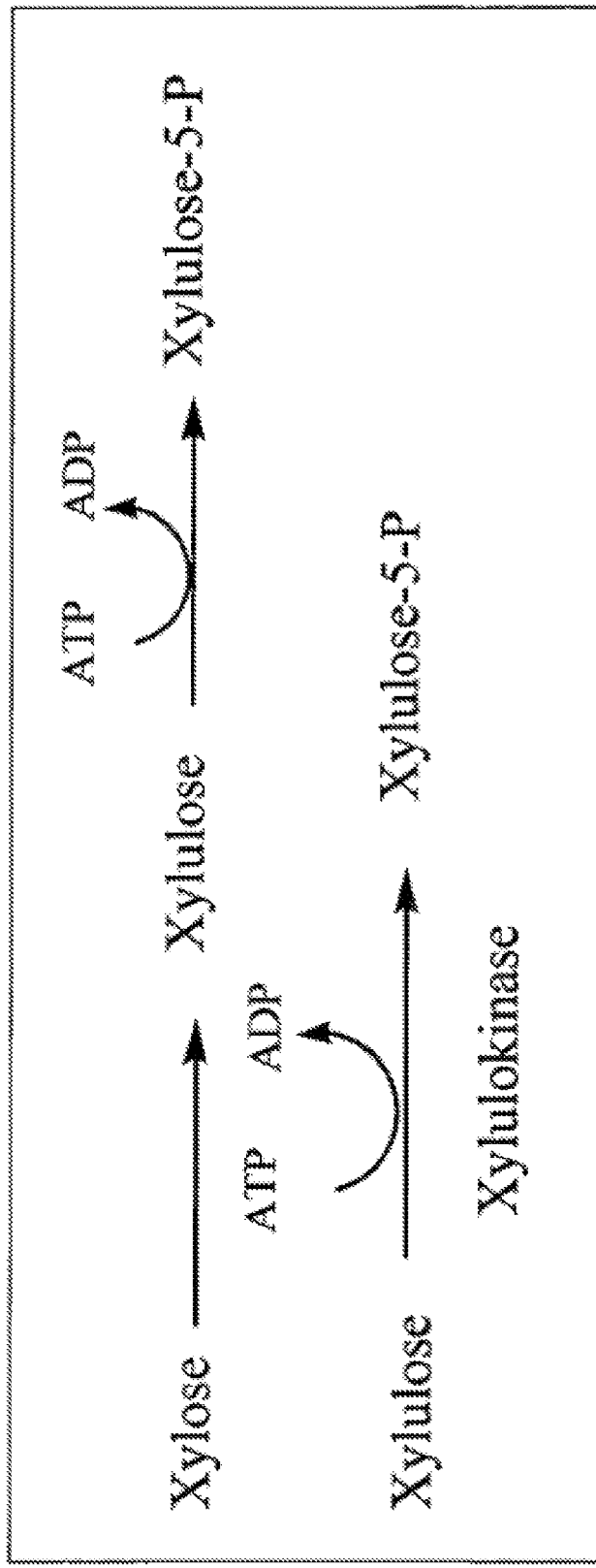
FIG. 2. Diagram of the conversion of D-xylose in recombinant *S. cerevisiae* by means of direct isomerization FIG. 3. Genealogical tree of the different xylose isomerases The genealogical tree of the tested xylose isomerases is depicted. Comparisons with regard to the similarity of the xylose isomerases were performed with the program "MEGA version 4".

Eadie-Hofstee Plot of the Xylose Conversion of the Native and the Codon-Optimized Xylose Isomerase from *C. phytofermentans*

The strain CEN.PK2-1C transformed with the plasmid p426H7-XI-Clos and p426H7-opt.XI-Clos, respectively, was grown over night in synthetic complete medium with 2% glucose and no uracil. Raw extracts were prepared and quantitative enzyme tests were performed. A representative result is shown. The values indicated in table 3 are average values from at least 3 independent measurements.

EXAMPLES

Methods
1. Strains and Media
    Bacteria
        *E. coli* SURE (Stratagene)
        *E. coli* DH5α (Stratagene)
        *Bacillus licheniformis* (37° C.)
        *Agrobacterium tumefaciens* (26° C.)
        *Burkholderia xenovorans* (28° C.)
        *Clostridium phytofermentans* (30° C., anaerobic)
        *Lactobacillus pentosus* (30° C.)
        *Leifsonia xyli* (28° C.)
        *Pseudomonas syringae pv. phaseolicola* (28° C.)
        *Robiginitalea biformata* (30° C.)
        *Saccharophagus degradans* (26° C.)
        *Salmonella typhimurium* LT2 (28° C.)
        *Staphylococcus xylosus* (37° C.)
        *Streptomyces diastaticus* (28° C.)
        *Xanthomonas campestris* (26° C.)
    Other Organisms
        *Arabidopsis thaliana* (genomic DNA)
    Media and Cultivation of *E. coli*
        Complete Medium LB:
            1% tryptone, 0.5% yeast extract, 0.5% NaCl, pH 7.5 (see Maniatis, 1982).
        For the selection for a plasmid-coded antibiotic resistance, 40 μg/ml of ampicillin was added to the medium after autoclaving. Solid culture media additionally contained 2% agar. The cultivation took place at 37° C.
    Media and Cultivation of Further Bacteria
        Composition of the media and cultivation conditions, see information from the DSMZ (Deutsche Sammlung von Mikroorganismen und Zellkulturen, Brunswick, Germany).
    Yeast
        Strain CEN.PK2-1C
        CEN.PK2-1C (MATa leu2-3, 112 ura3-52 trpl-289 his3-Δ1MAL2-8c SUC2)
        Strain MYKO9
        MKY09 is based on the strain CEN.PK2-1C (MATa leu2-3, 112 ura3-52 trpl-289 his3-Δ1MAL2-8C SUC2, PromTKL1::loxP-Prom-vkHXT7, PromRPE1::loxP-Prom-vkHXT7, PromRKI1::loxP-Prom-vkHXT7, Prom GAL2::loxP-Prom-vkHXT7, PromXKS1::loxP-Prom-vkHXT7), including further unknown mutations.

Media and Cultivation of Yeasts
Synthetic complete selective medium SC:
0.67% yeast nitrogen base w/o amino acids, pH 6.3, amino acid/nucleobase solution, carbon source in the concentration respectively given
Synthetic minimal selective medium SM:
0.16% yeast nitrogen base w/o amino acid and ammonium sulphate, 0.5% ammonium sulphate, 20 mM of potassium dihydrogenphosphate, pH 6.3, carbon source in the concentration respectively given
Concentration of the amino acids and nucleobases in the synthetic complete medium (according to Zimmermann, 1975): adenine (0.08 mM), arginine (0.22 mM), histidine (0.25 mM), isoleucine (0.44 mM), leucine (0.44 mM), lysine (0.35 mM), methionine (0.26 mM), phenylalanine (0.29 mM), tryptophan (0.19 mM), threonine (0.48 mM), tyrosine (0.34 mM), uracil (0.44 mM), valine (0.49 mM). L-arabinose and D-glucose were used as the carbon source.

2. Plasmids
Plasmids used

| Plasmid | Source/reference | Description |
| --- | --- | --- |
| p426HXT7-6HIS (=p426H7) | Hamacher et al., 2002 | 2μ expression plasmid for the overexpression of genes and for the production of a His$_6$ epitope; URA3 selection marker gene, truncated HXT7 promoter and CYC1 terminator |

Plasmids constructed in the course of this work

| Plasmid | Description |
| --- | --- |
| p426H7-XI-Agro | Cloning of the XI from *A. tumefaciens* in p426HXT7-6HIS omitting the His$_6$ epitope |
| p426H7-XI-Arab | Cloning of the XI from *A. thaliana* in p426HXT7-6HIS omitting the His$_6$ epitope |
| p426H7-XI-BaLi | Cloning of the XI from *B. licheniformis* in p426HXT7-6HIS omitting the His$_6$ epitope |
| p426H7-XI-Burk | Cloning of the XI from *B. xenovorans* in p426HXT7-6HIS omitting the His$_6$ epitope |
| p426H7-XI-Clos | Cloning of the XI from *C. phytofermentans* in p426HXT7-6HIS omitting the His$_6$ epitope |
| p426H7-opt.XI-Clos | Cloning of the codon-optimized XI from *C. phytofermentans* in p426HXT7-6HIS omitting the His$_6$ epitope |
| p426H7-XI-Lacto | Cloning of the XI from *L. pentosus* in p426HXT7-6HIS omitting the His$_6$ epitope |
| p426H7-XI-Leif | Cloning of the XI from *L. xyli* in p426HXT7-6HIS omitting the His$_6$ epitope |
| p426H7-opt.XI-Piro | Cloning of the codon-optimized XI from *Piromyces* sp. E2 in p426HXT7-6HIS omitting the His$_6$ epitope |
| p426H7-XI-Pseudo | Cloning of the XI from *P. syringae* in p426HXT7-6HIS omitting the His$_6$ epitope |
| p426H7-XI-Robi | Cloning of the XI from *R. biformata* in p426HXT7-6HIS omitting the His$_6$ epitope |
| p426H7-XI-Saccha | Cloning of the XI from *S. degradans* in p426HXT7-6HIS omitting the His$_6$ epitope |
| p426H7-XI-Salmo | Cloning of the XI from *S. typhimurium* in p426HXT7-6HIS omitting the His$_6$ epitope |
| p426H7-XI-Staph | Cloning of the XI from *S. xylosus* in p426HXT7-6HIS omitting the His$_6$ epitope |
| p426H7-XI-Strep | Cloning of the XI from *S. diastaticus* in p426HXT7-6HIS omitting the His$_6$ epitope |
| p426H7-XI-Xantho | Cloning of the XI from *X. campestris* in p426HXT7-6HIS omitting the His$_6$ epitope |

3. Transformation:
Transformation of *E. coli*
The transformation of *E. coli* cells was performed with the electroporation method according to Dower et al. (1988) and Wirth (1993) by means of an Easyject prima instrument (EQUIBO).

Transformation of *S. cerevisiae*
The transformation of *S. cerevisiae* strains with plasmid DNA or DNA fragments was performed in accordance with the lithium acetate method according to Gietz and Woods (1994).

4. Preparation of DNA
Isolation of plasmid DNA from *E. coli*
The isolation of plasmid DNA from *E. coli* was performed in accordance with the method of alkaline lysis according to Birnboim and Doly (1979), modified according to Maniatis et al. (1982) or alternatively with the "QIAprep Spin Miniprep Kit" from the company Qiagen.
High-purity plasmid DNA for sequencing was prepared with the "Plasmid Mini Kit" from the company Qiagen according to the manufacturer's instructions.
Isolation of Plasmid DNA from *S. cerevisiae*
The cells of a stationary yeast culture (5 ml) were harvested by centrifugation, washed and resuspended in 400 μl of buffer B1 (Plasmid Mini Kit, company Qiagen). Following the addition of 400 μl of buffer B2 and ⅔ of a volume of glass beads (Ø0.45 mm), the cell disruption was performed by shaking for 5 minutes on a Vibrax (Vibrax-VXR from Janke & Kunkel or IKA). ½ of a volume of buffer B3 was added to the supernatant, it was mixed and incubated for 10 min on ice. After centrifuging for 10 minutes at 13,000 rpm, the plasmid DNA was precipitated at room temperature by adding 0.75 ml of isopropanol to the supernatant. The DNA pelleted by centrifugation for 30 min at 13,000 rpm was washed with 70% ethanol, dried and resuspended in 20 μl of water. 1 μl of the DNA was used for the transformation in *E. coli*.
Colony PCR of *B. licheniformis* and *S. degradans*
Minor amounts of cells were collected from bacterial cultures growing on a plate by means of a toothpick and transferred into a PCR reaction vessel. Following the addition of H$_2$O, 0.2 mM dNTP mix, 1×PCR buffer (contains 1.5 mM MgCl$_2$) and in each case 10 pmol of the corresponding oligonucleotide primer, the cell disruption was performed in a thermocycler from the company Techne at 99° C. for 10 min. This batch was directly used in a PCR reaction as a template. By adding 1 U of polymerase, the polymerase chain reaction was started with a total volume of 50 μl.
Determination of the DNA Concentration
The DNA concentration was measured spectrophotometrically in a wavelength range of 240-300 nm. If the purity of the DNA, determined with the quotient $E_{260nm}/E_{280nm}$, is 1.8, the extinction $E_{260nm}=1.0$ corresponds to a DNA concentration of 50 μg of dsDNA/ml (Maniatis et al., 1982).
DNA Amplification by Means of PCR
Use of the Phusion™ High Fidelity Systems
The polymerase chain reaction was performed in a total volume of 50 μl with the "Phusion™ High Fidelity PCR System" from the company Finnzymes according to the manufacturer's instructions. Each batch consisted of 1-10 ng of DNA or 1-2 yeast gcolonies as the synthesis template, 0.2 mM of dNTP mix, 1× buffer 2 (contains 1.5 mM of MgCl$_2$), 1 U of polymerase and in each case 100 pmol of the corresponding oligonucleotide primer. The PCR reaction was performed in a thermocycler from the company Techne and the PCR conditions were chosen as follows, as required:

| 1. | 1× | 30 sec, 98° C. | Denaturation of the DNA |
| --- | --- | --- | --- |
| 2. | 30× | 10 sec, 98° C. | Denaturation of the DNA |
| | | 30 sec, 52-62° C. | Annealing/bonding of the oligonucleotides to the DNA |
| | | 50 sec, 72 | DNA synthesis/elongation |
| 3. | 1× | 7 min, 72° C. | DNA synthesis/elongation |

The polymerase was added after the first denaturation step ("hot-start PCR"). The number of synthesis steps, the annealing temperature and the elongation time were adapted to the specific melting temperatures of the oligonucleotides used or the size of the product to be expected, respectively. The PCR products were examined by means of an agarose gel electrophoresis and subsequently purified.

DNA Purification of PCR Products

The purification of the PCR products was performed with the "QIAquick PCR Purification Kit" from the company Qiagen according to the manufacturer's instructions.

Gel Electrophoretic Separation of DNA Fragments

The separation of DNA fragments having a size of 0.15-20 kb was performed in 0.5-1% agarose gels with 0.5 µg/ml of ethidium bromide. 1×TAE buffer (40 mM of Tris, 40 mM of acetic acid, 2 mM of EDTA) was used as the gel and running buffer (Maniatis et al., 1982). A lambda phage DNA cut with the restriction endonucleases EcoRI and HindIII served as a size standard. Before application, 1/10 of a volume of blue marker (1×TAE buffer, 10% glycerine, 0.004% bromophenol blue) was added to the DNA samples and they were visualized after the separation by irradiation with UV light (254 nm).

Isolation of DNA Fragments from Agarose Gels

The desired DNA fragment was cut out from the TAE agarose gel under long-wave UV light (366 nm) and isolated with the "QIAquick Gel Extraction Kit" from the company Qiagen according to the manufacturer's instructions.

5. Enzymatic Modification of DNA

DNA restriction

Sequence-specific cleavage of the DNA with restriction endonucleases was performed for 1 hour with 2-5 U of enzyme per µg of DNA under the incubation conditions recommended by the manufacturer.

6. Metabolite Analyses

Samples were taken at different times and centrifuged at 4° C. for 15 min at 13,000 rpm and 450 µl were collected from the supernatant. The protein precipitation was performed with 50% sulphosalicylic acid. 1/10 of a volume of sulphosalicylic acid was added onto the samples, mixed and centrifuged for 20 min at 13,000 rpm at 4° C. The supernatant was collected and the samples could be used for the measurement after another dilution with water. Samples with D-glucose, D-xylose, xylitol, acetate, glycerine and ethanol served as standards, which were employed in concentrations of 0.05% w/w, 0.1% w/v, 0.5% w/v, 1.0% w/v and 2.0% w/v.

The sugar concentration and the ethanol concentration were measured by means of BioLC (Dionex). The autosampler "AS50", the column heater "TCC-100", the RI detector "RI-101" (Shodex) and the gradient pump "GS50" were used in the measurement. The measurement of the samples was performed with the column VA 300/7.7 Nucleogel Sugar 810 H (Macherey-Nagel). The column was eluted at a temperature of 65° C. with 5 mM $H_2SO_4$ as the eluent and at a flow rate of 0.6 ml·min$^{-1}$. The evaluation of the data was performed with the program Chromeleon Version 6.50™ (version 6.50, Dionex).

7. Measurement of Enzyme Activities in *S. cerevisiae*

Preparation of Raw Extracts 50 ml of cultures of yeast cells were grown to the exponential phase in synthetic minimal medium with 2% glucose. The cells were harvested, washed twice in Tris-HCl buffer (pH 7.5) and disrupted by means of glass beads (Ø=0.45 nm) for 8 min on a Vibrax (Janke & Kunkel, Vibrax-VBR) at 4° C. Cell debris was removed by centrifugation for 10 min at 13,000 rpm. Subsequently, the supernatant was collected and filled up to 2 ml with cold Tris-HCl buffer (pH 7.5) and used as a raw extract for the protein determination and for the measurement of the enzyme activities or the xylitol inhibition.

Protein Determination

The protein concentration was determined with the kit "Roti-Quant" from the company Carl Roth GmbH+Co. according to the manufacturer's instructions on the basis of Bradford (1976). In this connection, bovine serum albumin (BSA) in concentrations of 0-100 µg/ml served as the standard. After an incubation time of at least 5 min at room temperature, the samples were measured in microtiter plates with a microtiter plate photometer from the company Molecular Devices at $OD_{590}$.

Measurement of the Xylose Isomerase Activity

To determine the xylose isomerase activity, recombinant yeast cells containing the vector p426H7-XI-Clos or p426H7-opt.XI-Clos, respectively, were grown, harvested and raw extracts were prepared. Recombinant yeast cells containing the empty vector p426HXT7-6HIS served as a comparison. In a total volume of 1 ml, the conversion of 6.25-500 mM of xylose with 100 µl of raw extract, 0.23 mM of NADH, 10 mM of $MgCl_2$, 2 U of sorbitol dehydrogenase in 100 mM of Tris-HCl buffer (pH 7.5) was continuously monitored. The acceptance of NADH as a measured variable was determined spectrophotometrically at a wave length of 340 nm. The reaction was started by adding xylose.

Measurement of the Xylitol Inhibition

To determine the xylitol inhibition of the xylose isomerase recombinant yeast cells containing the vector p426H7-XI-Clos were grown, harvested and raw extracts were prepared. Recombinant yeast cells with the vector p426H7-opt.XI-Piro or the vector p426HXT7-6HIS, respectively, served as a comparison. In a total volume of 1 ml, the conversion of 6.25-500 mM of xylose with 100 µl of raw extract, 10-100 mM of xylitol, 0.23 mM of NADH, 10 mM of $MgCl_2$, 2 U of sorbitol dehydrogenase in 100 mM of Tris-HCl buffer (pH 7.5) was continuously monitored. The acceptance of NADH as a measured variable was determined spectrophotometrically at a wave length of 340 nm. The reaction was started by adding xylose.

Example 1: Screen of a (Highly) Functional Prokaryotic Xylose Isomerase

A) Construction of MKY09

In the yeast strain CEN.PK2-1C, all the genes of the non-oxidative pentose phosphate pathway as well as the xylulokinase (XKS1) and GAL2 were overexpressed. To this end, the endogenous promoters were replaced with the truncated HXT7 promoter. This strain was named MKY09 and used for the screen for functional xylose isomerases.

B) Selection of the Xylose Isomerases to be Tested

Figure 3:
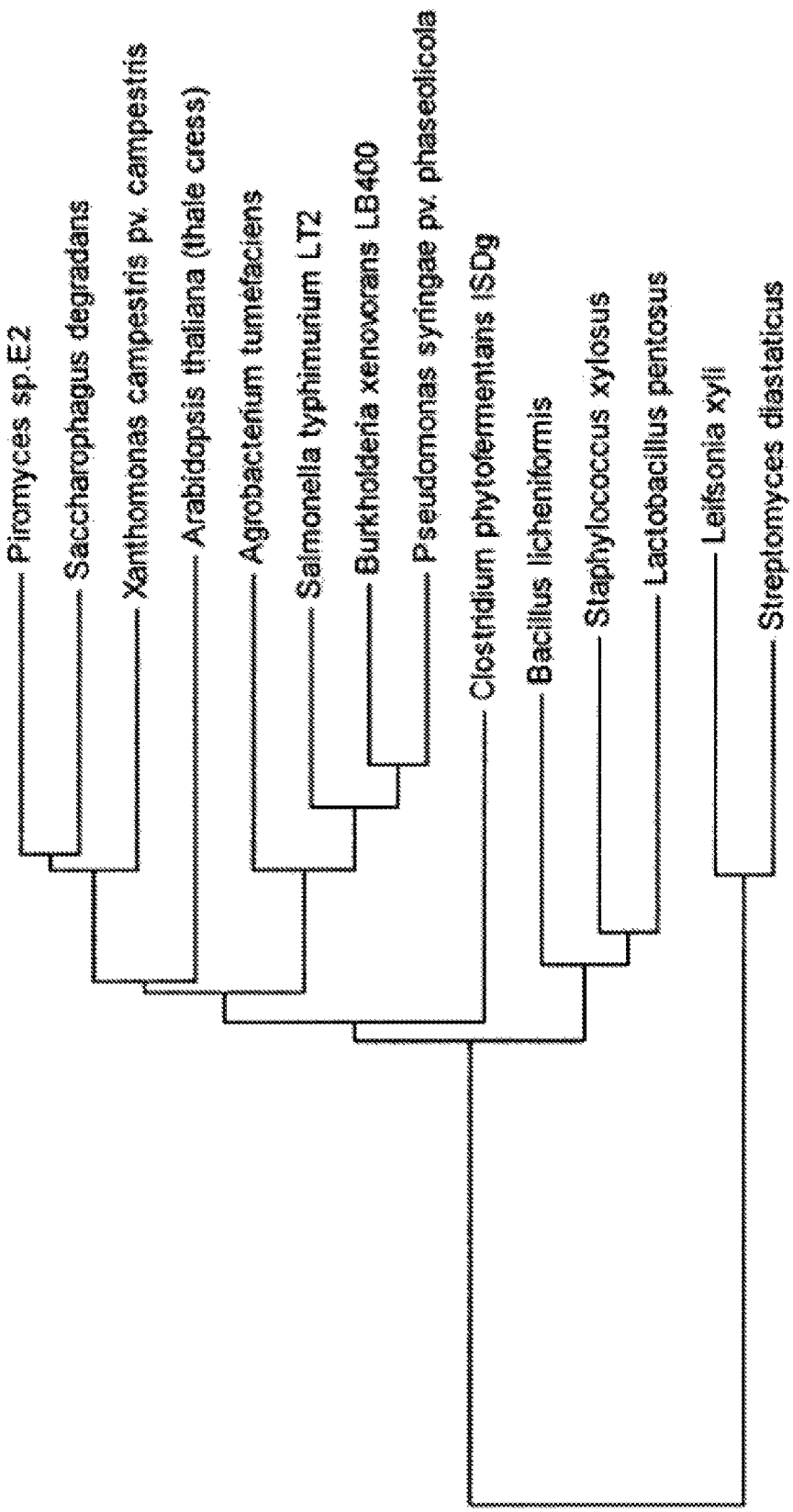

To make a selection of the xylose isomerases to be tested, protein sequences of xylose isomerases from the database NCBI BLAST were compared. An excerpt of the xylose isomerase obtained is depicted in FIG. 3. 14 xylose isomerases from different organisms were selected to be tested on their functionality in yeast.

C) Execution of the Screen

To this end, genomic DNA was isolated from the organisms. The cells were grown, harvested and disrupted (see "Isolation of plasmid DNA from *S. cerevisiae*" and "Colony PCR from *B. licheniformis* and *S. degradans*", respectively). The open reading frame (ORF) of XI from the mentioned organisms was amplified with primers additionally having homologous regions to the HXT7 promoter or CYC1 terminator.

Figure 4A:
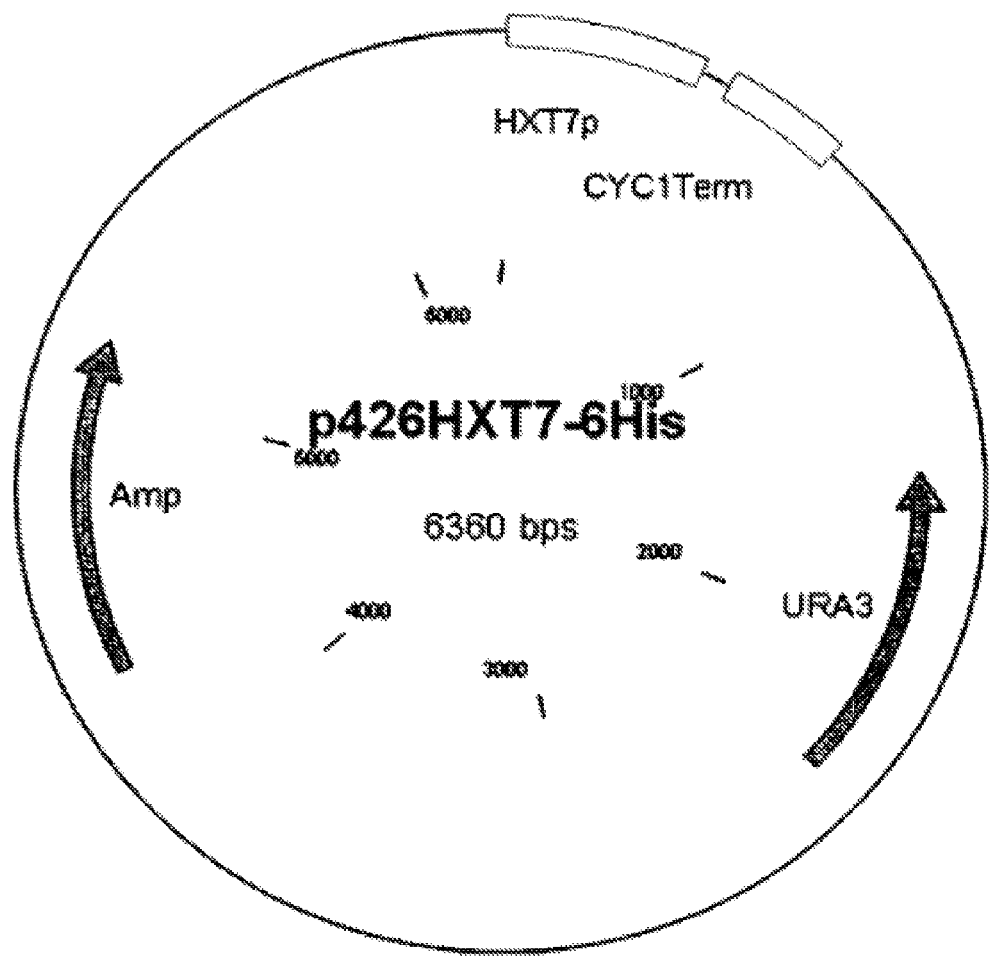
FIGS. 4A-4C. Used vectors. The starting plasmid for the construction of p426H7-XI-Clos (4B) or p426H7-opt.XI-Clos (4C) was the plasmid p426HXT7-6HIS (4A). Vector p426HXT7-6HIS is a 2μ expression plasmid, which has a URA3 marker. The open reading frame (ORF) and its codon-optimized form of the xylose isomerase from *C. phytofermentans* according to the invention, respectively, was cloned behind the truncated strong HXT7 promoter and the CYC1 terminator of the plasmid p426HXT7-6HIS.
Figure 4B:
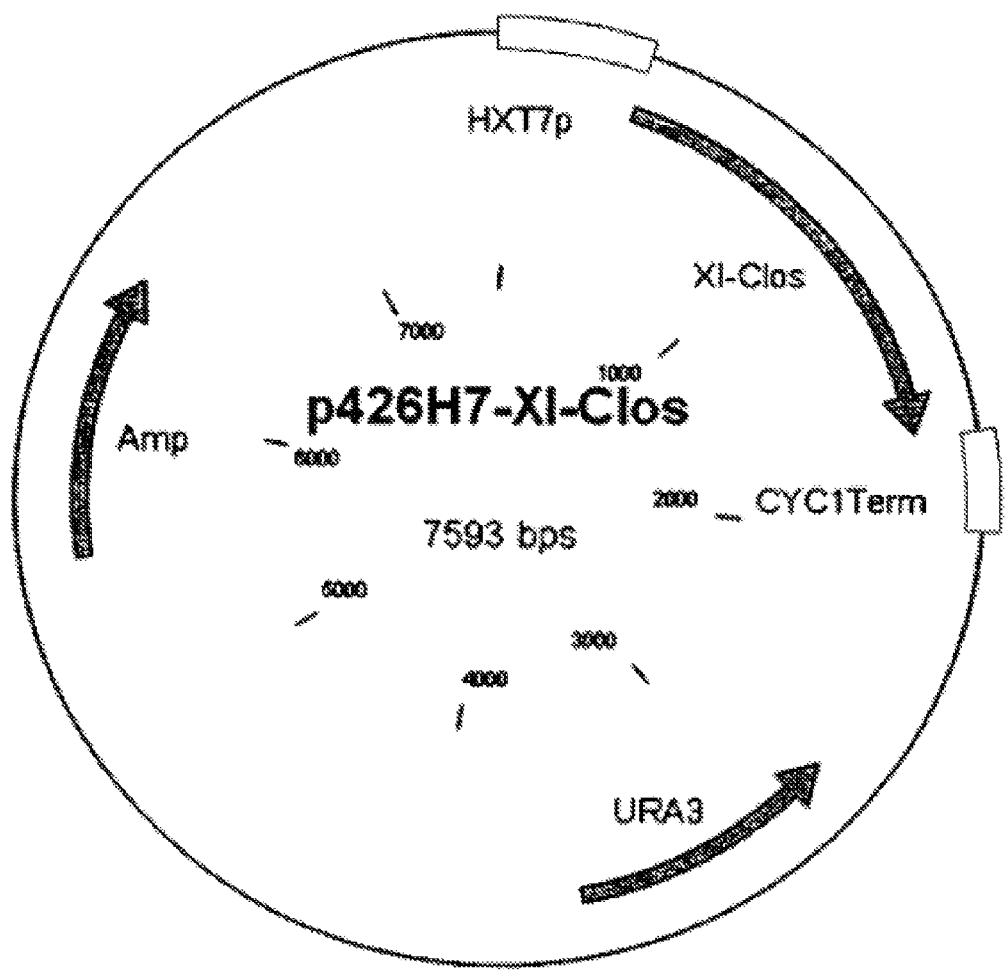
Figure 4C:
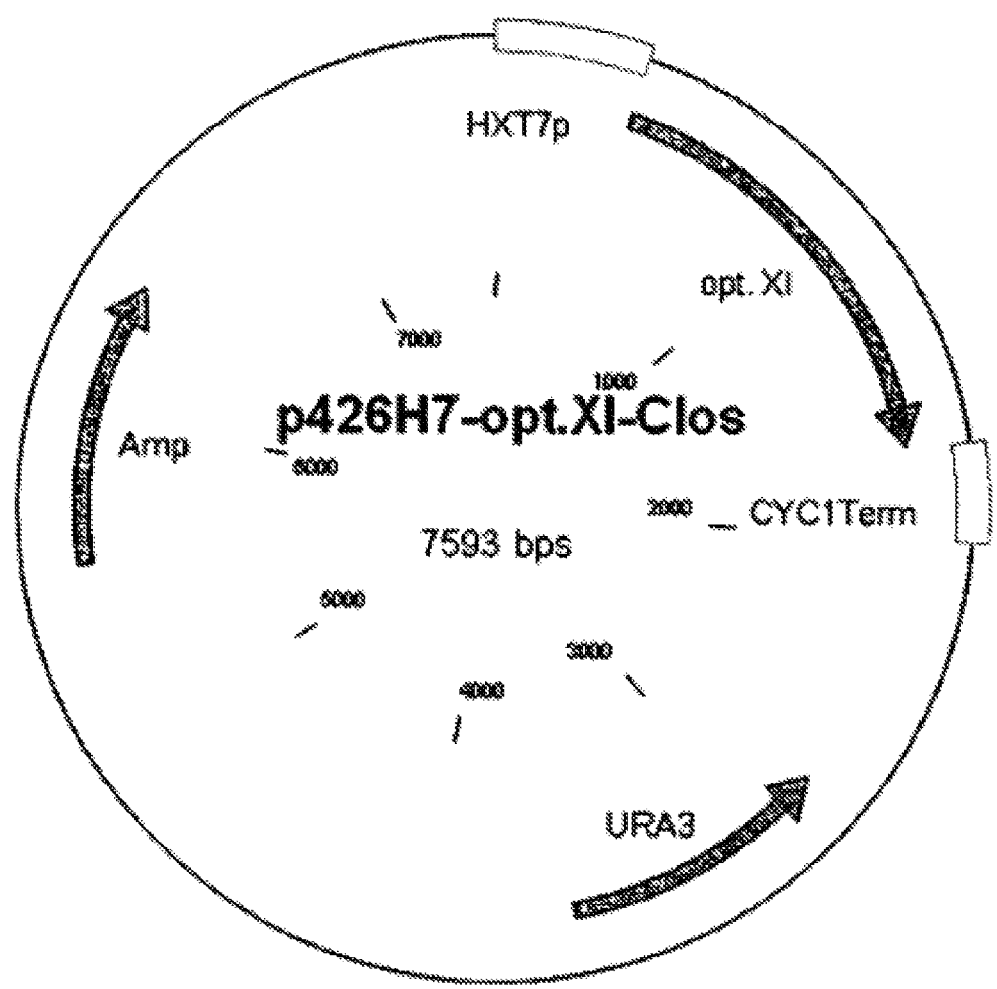

The obtained PCR products were together with the vector p426HXT7-6HIS linearized with EcoRI/BamHI transformed in yeast and cloned via in vivo recombination into the plasmid between the HXT7 promoter or CYC1 terminator, respectively (FIG. 4). The sequence of the plasmids obtained was verified by means of restriction analysis. Furthermore, the functionality of the new isomerases and its effect on the xylose conversion in yeast was to be studied. However, it was not possible to amplify the desired PCR product with the xylose isomerase from the organisms *Streptomyces diastaticus* and *Leifsonia xyli*. Both xylose isomerases thus could not be tested on functionality in yeast.

D) Growth Behaviour (Plate)

Figure 5C:
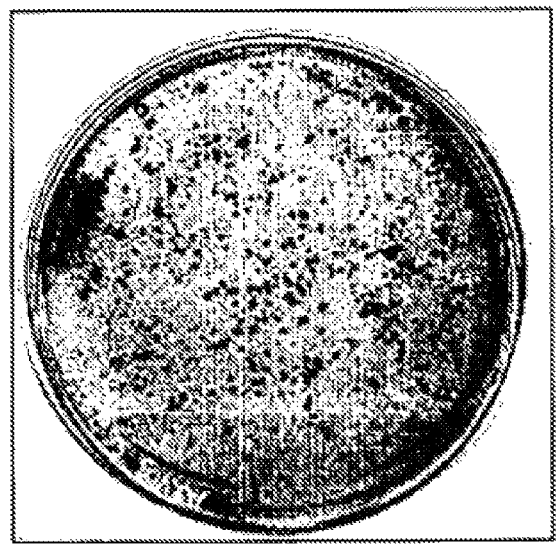
FIG. 5A-5C. Growth behaviour on medium containing xylose using the different xylose isomerase genes Growth tests of recombinant *S. cerevisiae* strains, which include the bacterial D-xylose metabolism with the xylose isomerase from *C. phytofermentans*. Growth tests were performed on agar plates with SC medium and 2% xylose as the only carbon source. The native (5B) and the codon-optimized form (5C) of the xylose isomerase from *C. phytofermentans* were tested. The empty vector p426HXT7-6HIS (5A) served as the negative control.
Figure 5B:
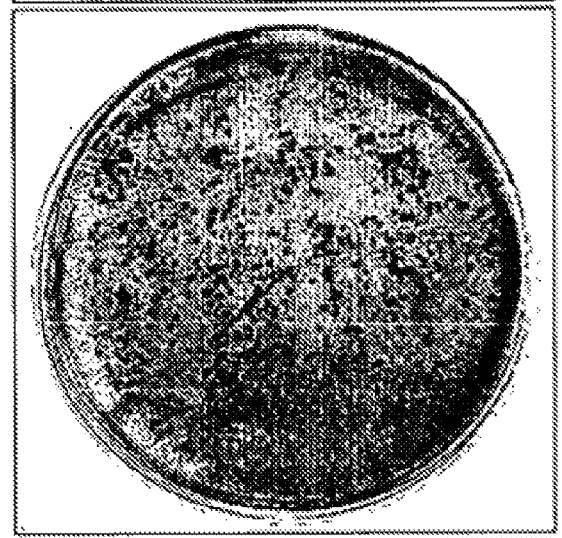
Figure 5A:
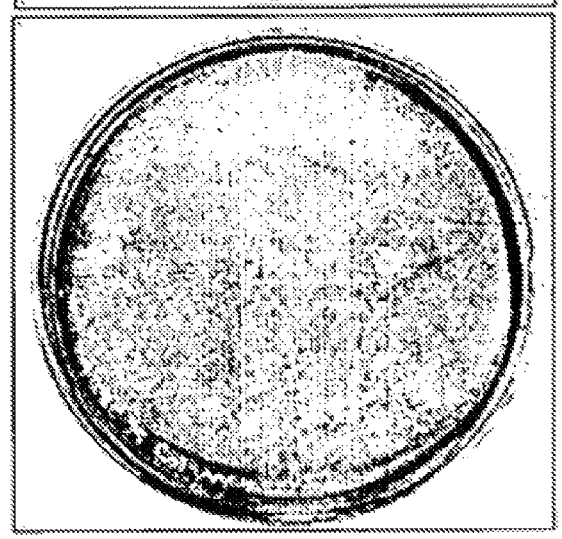

Out of the 12 different tested xylose isomerases, a xylose isomerase was found, which was functional in yeast strain MKY09. Recombinant yeasts containing the xylose isomerase from *C. phytofermentans* showed good growth on plates containing xylose (FIG. 5).

Example 2: Codon Optimization of the Gene for Xylose Degradation in Yeast Codon Optimization of Genes According to the Codon Usage of the Glycolysis Genes from *S. cerevisiae*

The preferred codon usage of the glycolysis genes from *S. cerevisiae* was determined and is listed in table 1. The ORF of the gene XI from *C. phytofermentans* was codon-optimized. That is, the sequences of the open reading frame were adapted to the preferred codon usage indicated below. The protein sequence of the enzymes remained unchanged. The genes were synthesized by an external company and supplied in dried form in company-owned vectors. Further details about the synthesis of genes can be found under www.geneart.com.

TABLE 1

Preferred codon usage of the glycolytic genes from *S. cerevisiae*

| Amino acid | Codon usage of codon-optimized genes |
|---|---|
| Ala | GCT |
| Arg | AGA |
| Asn | AAC |
| Asp | GAC |
| Cys | TGT |
| Gln | CAA |
| Glu | GAA |
| Gly | GGT |
| His | CAC |
| Ile | ATT |
| Leu | TTG |
| Lys | AAG |
| Met | ATG |
| Phe | TTC |
| Pro | CCA |
| Ser | TCT |
| Thr | ACC |
| Trp | TGG |
| Tyr | TAC |
| Val | GTT |
| Stop | TAA |

B) Introduction of the Codon-Optimized Xylose Isomerase Gene into the Strain MKY09

To test the codon-optimized xylose isomerase gene in strain MKY09, the gene had to be subcloned into a yeast vector. To this end, the codon-optimized XI-ORF was amplified with primers and cloned into the linearized vector p426HXT7-6HIS (see "Execution of the screen"). The sequence of the obtained plasmid p426H7-opt.XI-Clos was verified by means of restriction analysis. To test the functionality of the codon-optimized isomerase, the plasmid p426H7-opt.XI-Clos was transformed in the strain MKY09. Recombinant yeast strains showed good growth on plates with medium containing xylose (FIG. 5). Further characterizations of the native and the codon-optimized XI from *C. phytofermentans* followed.

Example 3: Characterization of the Functional Prokaryotic Xylose Isomerase

A) Growth Behaviour and Xylose Conversion

The growth of the strain MKY09 with the native and the codon-optimized xylose isomerase from *C. phytofermentans* was investigated in growth tests on medium containing xylose under aerobic conditions. The empty vector p426HXT7-6HIS served as a comparison.

The strains were grown in SC medium with 0.1% glucose and 1.4% xylose and inoculated with an $OD_{600nm}=0.2$ in 50 ml of SC medium with 0.1% glucose and 1.4% xylose. The incubation was performed in shaking flasks under aerobic conditions at 30° C. Samples for the determination of the optical density and for the determination of the metabolite composition were taken several times.

The growth curves showed that all the recombinant yeasts grew on glucose up to an $OD_{600}$ of 2.5 (table 2). After another 50 h, the yeast strain containing the native xylose isomerase from *C. phytofermentans* began to grow further on xylose and reached a final $OD_{600}$ of 3.5 at a maximum growth rate of 0.0058 $h^{-1}$ on medium containing xylose. The yeast strain with the codon-optimized xylose isomerase likewise reached a final $OD_{600}$ of 3.5. The maximum growth rate was 0.0072 $h^{-1}$. Yeast transformants with the empty vector p426HXT7-6HIS showed no growth on xylose and began to die already after 150 h.

Figure 6:
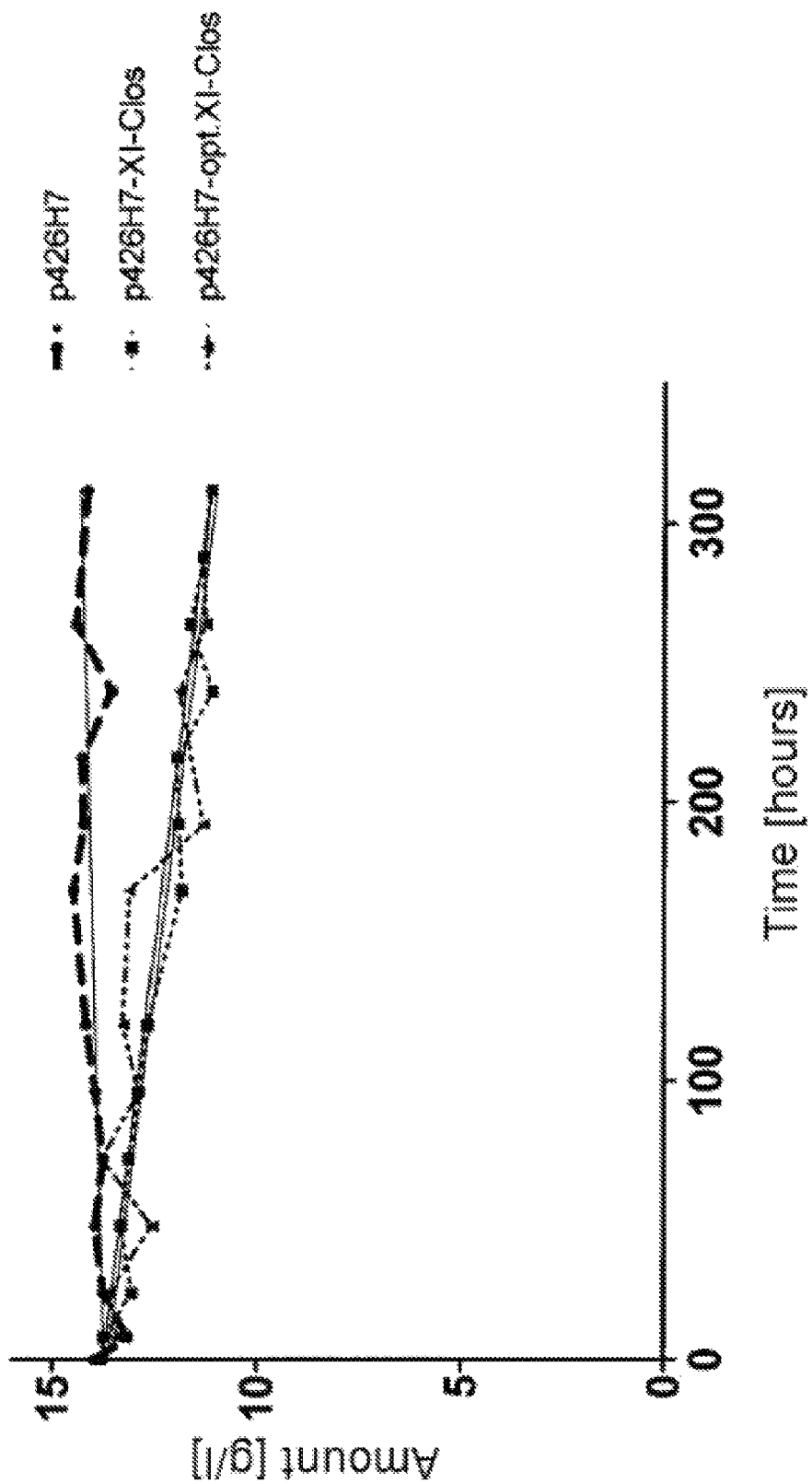
FIG. 6. Xylose conversion in recombinant yeast strains using a bacterial xylose isomerase The xylose conversion of recombinant yeast cells MKY09, which contained the native and the codon-optimized form of the xylose isomerase from *C. phytofermentans* was tested. The empty vector p426HXT7-6HIS served as a comparison. Growth curves were performed in liquid SC medium with 1.4% xylose under aerobic conditions. HPLC samples were taken in parallel to measure the optical density at 600 nm. See also table 2, example 3.

The recombinant yeasts containing the native xylose isomerase from *C. phytofermentans* or the codon-optimized xylose isomerase, respectively, converted more than 2.6 g of xylose in 312 hours (FIG. 6).

TABLE 2

Determination of the maximum growth rate on xylose (µ)

| MKY09 transformed with plasmid | Max. growth rate |
|---|---|
| p426H7-XI-Clos | 0.0058 |
| p426H7-opt.XI-Clos | 0.0072 |

It could be shown with this experiment that the introduction of the native as well as the codon-optimized xylose isomerase from *C. phytofermentans* allows the recombinant *S. cerevisiae* strains growth on D-xylose and its conversion. By means of the codon optimization of the xylose isomerase, a higher max. growth rate could be achieved.

B) Measurement of the Xylose Isomerase Activity

Enzyme tests were performed directly after the raw extract preparation. The XI activity was performed at 30° C. in a reaction mix (100 mM of Tris-HCl, pH 7.5; 10 mM of $MgCl_2$, 0.23 mM of NADH; 2 U of sorbitol dehydrogenase) with different raw extract concentrations. The reaction was started with 6.25-500 mM of xylose.

Figure 7:
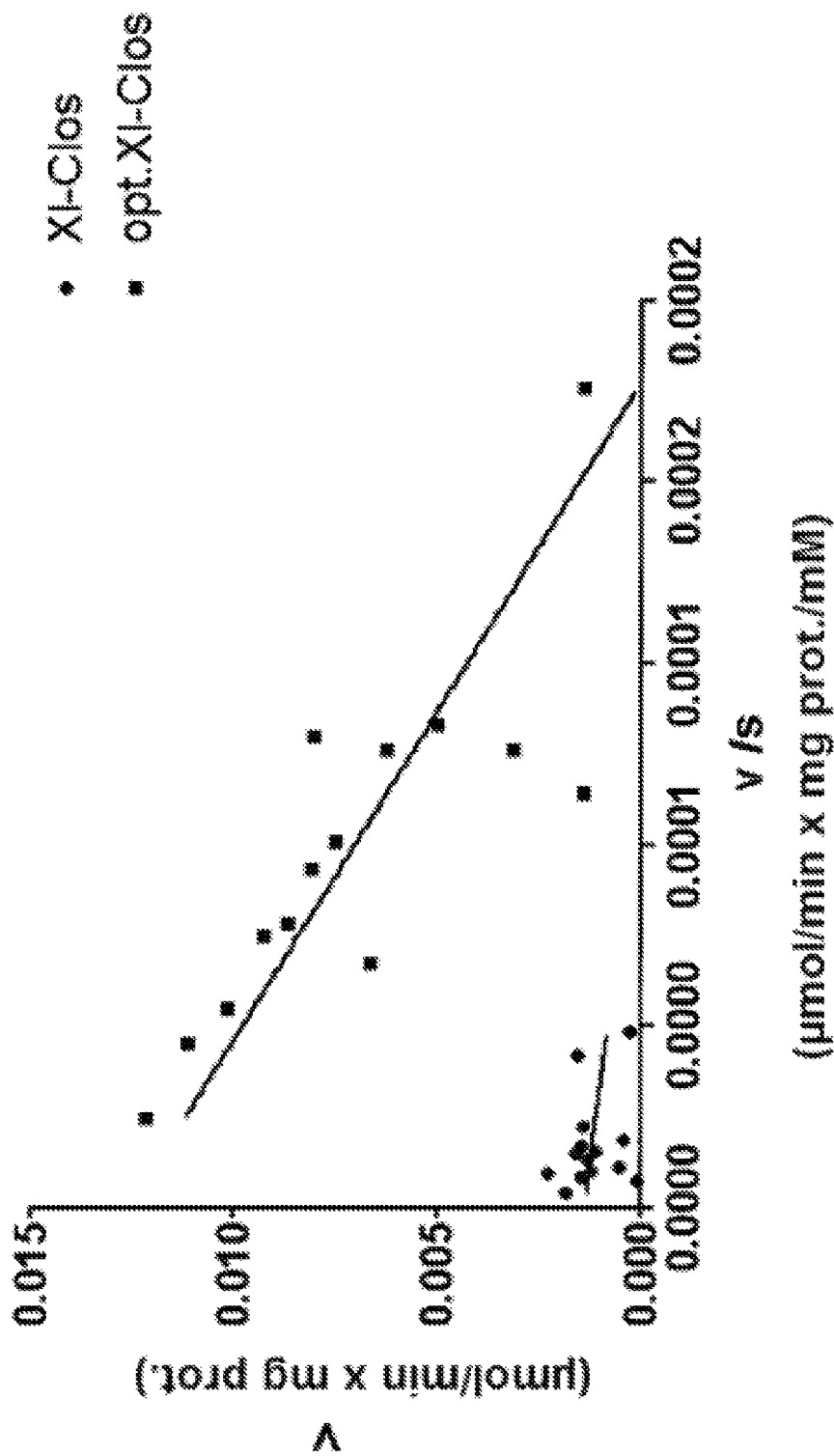
FIG. 7. Enzyme kinetics

The determination of the enzyme kinetics of the native form of the xylose isomerase resulted in a $K_m$ value of 61.85±3.41 mM and for the codon-optimized form a $K_m$ value of 66.01±1 mM (FIG. 7 and table 3). As expected, the $K_m$ values were thus the same as they do not differ significantly.

$V_{max}$ (μmol/min$^{-1}$ mg protein$^{-1}$) was 0.0076 for the native form of the xylose isomerase and 0.0344 for the codon-optimized form (FIG. 7). Therefore, $V_{max}$ could be increased by more than 450% by means of the codon optimization of the enzyme.

TABLE 3

| CEN.PK2-1C transformed with plasmid | $V_{max}$ (μmol/min$^{-1}$ protein$^{-1}$) mg | $K_m$ (mM) |
|---|---|---|
| p426H7-XI-Clos | 0.0076 | 61.85 ± 3.4 |
| p426H7-opt.XI-Clos | 0.0344 | 66.01 ± 1 |

The strain CEN.PK2-1C transformed with the plasmid p426H7-XI-Clos and p426H7-opt.XI-Clos, respectively, was grown over night in synthetic complete medium with 2% glucose and no uracil. Raw extracts were prepared and quantitative enzyme tests were performed.

C) Measurement of the Xylitol Inhibition

The determination of the xylitol inhibition of the xylose isomerases was performed directly after the raw extract preparation. The XI activity was performed at 30° C. in a reaction mix (100 mM of Tris-HCl, pH 7.5; 10 mM of MgCl$_2$, 0.23 mM of NADH; 2 U of sorbitol dehydrogenase) with different raw extract concentrations. Additionally, different concentrations of xylitol (10-100 mM) were present in the reaction mix. The reaction was started with 6.25-500 mM of xylose.

K was determined via the equation $K_m'=K_m'=K_m*(1+i/K_i)$, i being the xylitol concentration used and $K_m'$ being the apparent $K_m$ value at the corresponding xylitol concentration.

The determination of the kinetics of the xylitol inhibition of the xylose isomerase form C. phytofermentans resulted in a $K_i$ value of 14.24±1.48 mM (table 4). As already described several times (Yamanaka et al., 1969 and references cited therein), it is a competitive inhibition.

TABLE 4

| CEN.PK2-1C transformed with plasmid | $K_i$ (mM) |
|---|---|
| p426H7-opt.XI-Piro | 4.67 ± 1.77 |
| p426H7-opt.XI-Clos | 14.51 ± 1.08 |

The strain CEN.PK2-1C transformed with the plasmid p426H7-opt.XI-Clos and p426H7-opt.XI-Piro, respectively, was grown over night in synthetic complete medium with 2% glucose and no uracil. Raw extracts were prepared and quantitative enzyme tests with constant xylitol concentrations of 10-100 mM were performed.

The xylose isomerase from Piromyces sp.E2 and the empty vector p426HXT7-6HIS served as a comparison. The determined $K_i$ value of the xylose isomerase from Piromyces sp.E2 was 4.67±1.77 mM.

It can be seen from the determined $K_i$ values that the xylose isomerase from C. phytofermentans is significantly less inhibited by xylitol than the xylose isomerase from Piromyces sp.E2.

D) Examples of Vectors for the Xylose Isomerase

The plasmid p426HXT7-6HIS was the starting plasmid for the construction of p426H7-opt.XI-Clos. The vector is a 2μ expression plasmid, which has a URA3 marker.

Further possible expression vectors are from the series of pRS303X, p3RS305× and p3RS306X. These are integrative vectors, which have a dominant antibiotic marker. Further details about these vectors can be found in Taxis and Knop (2006).

REFERENCES

Amore, R., Wilhelm, M. and Hollenberg, C. P. (1989)
The fermentation of xylose—an analysis of the expression of Bacillus and Actinoplanes xylose isomerase genes in yeast.
Appl. Microbiol. Biotechnol. 30:351-357

Banerjee, S., Archana, A. and Satyanarayana, T. (1994)
Xylose metabolism in a thermophilic mould Malbranchea pulchella var. sulfurea TMD 8. Curr. Microbiol. 29:349-352

Birnboim, H. C. and Doly, J. (1979)
A rapid alkaline extraction procedure for screening recombinant plasmid DNA. Nucl. Acids Res. 7: 1513-1523

Dower, W. J., Miller, J. F. and Ragsdale, C. W. (1988)
High efficiency transformation of E. coli by high voltage electroporation. Nucl. Acids Res. 16: 6127-6145

Eliasson, A., Christensson, C, Wahlbom, C. F. and Hahn-Hägerdal, B. (2000)
Anaerobic xylose fermentation by recombinant Saccharomyces cerevisiae carrying XYL1, XYL2 and XKSI in mineral medium chemostat cultures.
Appl. Environ. Microbiol. 66: 3381-3386

Gárdonyi, M. and Hahn-Hägerdahl, B. (2003)
The Streptomyces rubigniosus xylose isomerase is misfolded when expressed in Saccharomyces cerevisiae.
Enzym. Microb. Technol. 32, 252-259

Gietz, R. D. and Woods, R. A. (1994)
High efficiency transformation in yeast.
In: Molecular Genetics of Yeast: Practical Approaches, J. A. Johnston (Ed.).
Oxford University Press, pp. 121-134

Hahn-Hägerdal, B., Wahlborn, C F., Gárdonyi, M., van Zyl, W., Otero, R. R. C. and Jönsson, L. J. (2001)
Metabolic engineering of Saccharomyces cerevisiae for xylose utilization.
Adv. Biochem. Eng. Biotechnol. 73:53-84

Harhangi, H. R. (2003)
Xylose metabolism in the anaerobic fungus Piromyces sp. Strain E2 follows the bacterial pathway.
Arch Microbiol. 180:134-141.

Hayn, M., Steiner, W., Klinger, R., Steinmuller, H., Sinner, M. and Esterbauer, H. (1993)
Basic research and pilot studies on the enzymatic conversion of lignocellulosics. In Bioconversion of forest and agricultural plant residues, ed. Saddler, J. N. (CAB international, Wallingford, UK), pp. 33-72.

Ho, N. W. Y., Chen, Z. and Brainard, A. P. (1998)
Genetically engineered Saccharomyces yeast capable of effective cofermentation of glucose and xylose.
Appl. Environ. Microbiol. 64:1852-1859

Kotter, P. and Ciriacy, M. (1993)
Xylose fermentation by Saccharomyces cerevisiae. Appl. Microbiol. Biotechnol. 38:776-783

Kyper, M. Harhangi, H. R., Stave, A. K., Winkler, A. A., Jetten, M. S., de Laat, W. T., den Ridder, J. J. J., Op den Camp, H. J., van Dijken, J. P. and Pronk, J. T. (2003)

High-level functional expression of a fungal xylose isomerase: the key to efficient ethanolic fermentation of xylose by *Saccharomyces cerevisiae?*
*FEMS Yeast Res.* 4:69-78

Maniatis T, Fritsch, E. F and Sambrook, J. (1982)
Molecular cloning. A laboratory manual.
Cold Spring Harbor Laboratory, New York.

Metzger, M. H. and Hollenberg, C. P. (1994)
Isolation and characterization of the *Pichia stipitis* transketolase gene and expression in a xylose-utilising *Saccharomyces cerevisiae* transformant. *Appl. Microbiol. Biotechnol.* 42:319-325

Moes, J. M., Pretorius, I. S. and van Zyl, W. H. (1996)
Cloning and expression of the *Clostridium thermosulfurogenes* D-xylose isomerase gene (xylA) in *Saccharomyces cerevisiae*
*Biotechnol. Lett.* 18: 269-274.

Rawat, U., Phadthare, S., Deshpande, V. and Rao, M. (1996)
A novel xylose isomerase from *Neurospora crassa.*
*Biotechnol. Lett.* 18:1267-1270

Sarthy A. V., McConaughy B. L., Lobo Z., Sundstrom J. A., Furlong C. E., Hall B. D.
Expression of the Escherichia coli xylose isomerase gene in *Saccharomyces cerevisiae.*
*Appl Environ Microbiol.* 1987 September; 53(9): 1996-2000

Schaaff-Gerstenschläger, I. and Miosga, T. (1997)
The pentose phosphate pathway. In: Yeast Sugar Metabolism: Biochemistry, Genetics, Biotechnology, and Applications. Zimmermann, F. K. and Entian K.-D (Ed.), Chapter 15. Technomic, Lancaster, Pa.

Taxis, C. and Knop, M. (2006)
System of centromeric, episomal, and integrative vectors based on drug resistance markers for *Saccharomyces cerevisiae.*
*Bio Techniques* 40, No. 1

Tomoyeda, M. and Horitsu, H. (1964)
Pentose metabolism in *Candida utilis* Part I: Xylose isomerase.
*Agric. Biol. Chem.* 28:139-143.

Vongsuvanglert, V. and Tani, Y. (1988)
Purification and characterisation of xylose isomerase of a methanol yeast, *Candida boidinii,* which is involved in sorbitol production from glucose.
*Agric. Biol. Chem.* 52:1818-1824.

Yamanaka, K. (1969)
Inhibition of D-xylose isomerase by pentitols and D-lyxose.
*Arch. Biochem. Biophys.* 131, 502-506.

Zimmermann, F. K. (1975)
Procedures used in the induction of mitotic recombination and mutation in the yeast *Saccharomyces cerevisiae.* Mutation Res. 31:71-81.

---

We claim:

1. A method for the recombinant expression and production of a functional xylose isomerase or for the conversion of xylose to xylulose by an isolated host cell, wherein said isolated host cell is a yeast cell selected from the group consisting of *Saccharomyces cerevisiae, Saccharomyces bulderi, Saccharomyces barnetti, Saccharomyces exiguus, Saccharomyces uvarum, Saccharomyces diastaticus, Kluyveromyces lactis, Kluyveromyces marxianus,* and *Kluyveromyces fragilis,* and wherein said method comprises transforming said host cell with a nucleic acid molecule comprising a nucleic acid sequence that encodes a *Clostridium phytofermentans* xylose isomerase (XI) having an amino acid sequence that is at least 95% identical to the amino acid sequence SEQ ID NO: 1.

2. The method according to claim 1, wherein said method is used for:
   the conversion or metabolization of biomaterial containing xylose,
   the production of bio-based chemicals, or
   the production of biobutanol, bioethanol or of both biobutanol and bioethanol.

3. The method according to claim 1, wherein the nucleic acid molecule is a nucleic acid expression construct, which comprises promoter and terminator sequences, the promoter being operatively linked with the nucleic acid sequence encoding the *Clostridium phytofermentans* xylose isomerase (XI).

4. The method according to claim 3, wherein the nucleic acid expression construct further comprises one or more of 5' recognition sequences, 3' recognition sequences, and selection markers.

5. An isolated host cell, wherein said host cell is a yeast cell selected from the group consisting of *Saccharomyces cerevisiae, Saccharomyces bulderi, Saccharomyces barnetti, Saccharomyces exiguus, Saccharomyces uvarum, Saccharomyces diastaticus, Kluyveromyces lactis, Kluyveromyces marxianus,* and *Kluyveromyces fragilis,* and said host cell is transformed with a nucleic acid expression construct comprising:
   (a) a nucleic acid sequence encoding a *Clostridium phytofermentans* xylose isomerase (XI), having an amino acid sequence that is at least 95% identical to the amino acid sequence SEQ ID NO: 1, and said nucleic acid sequence being operatively linked to a promoter allowing for the expression of the *Clostridium phytofermentans* xylose isomerase (XI) in the cell; or
   (b) a nucleic acid sequence that is at least 95% identical to the nucleic acid sequence of SEQ ID NO: 2 and which is operatively linked to a promoter allowing for the expression of the *Clostridium phytofermentans* xylose isomerase (XI) in the cell,
   wherein the expression of the nucleic acid expression construct produces a functional xylose isomerase in the host cell and imparts to the host cell the capability to isomerize xylose into xylulose.

6. The isolated host cell according to claim 5, wherein the cell is transformed with a nucleic acid expression vector that is a nucleic acid expression construct, which comprises promoter and terminator sequences, the promoter being operatively linked with the nucleic acid sequence coding for a *Clostridium phytofermentans* xylose isomerase (XI), said nucleic acid sequence being at least 95% identical to the nucleic acid sequence SEQ ID NO: 2; wherein the nucleic acid expression construct optionally further comprises 5' and/or 3' recognition sequences and/or selection markers.

7. The isolated host cell according to claim 5, wherein the cell further expresses one or more enzymes that impart to the cell the capability to produce further metabolization products,
   the further metabolization products being selected from lactic acid, acetic acid, succinic acid, malic acid, 1-butanol, isobutanol, 2-butanol, other alcohols, amino acids, 1,3-propanediol, ethylene, glycerol, a β-lactam antibiotic or a cephalosporin, alkanes, terpenes, isoprenoids and the precursor molecule amorphadiene of the antimalarial drug artemisinin.

8. A method for the conversion and metabolization of biomaterial containing xylose to ethanol or for the production of bioethanol wherein said method utilizes a cell of claim 5; and wherein the ethanol yield is at least 0.3 g of ethanol per g of xylose.

9. A method for the production of a metabolization product, wherein said method utilizes a cell according to claim 5 and wherein
   the metabolization product is selected from lactic acid, acetic acid, succinic acid, malic acid, 1-butanol, isobutanol, 2-butanol, other alcohols, amino acids, 1,3-propanediol, ethylene, glycerol, a β-lactam antibiotic or a cephalosporin, alkanes, terpenes, isoprenoids and the precursor molecule amorphadiene of the antimalarial drug artemisinin.

10. The method for the production of bioethanol according to claim 8 comprising the steps of:
    (a) converting a medium containing a xylose source with said cell, which converts xylose to ethanol,
    (b) optionally obtaining the ethanol.

11. The method according to claim 10, wherein the medium contains a further carbon source.

12. The method according to claim 10, wherein the production of bioethanol takes place at a rate of at least 0.03 g of ethanol per g of yeast dry weight an hour.

13. A method for the production of a metabolization product comprising the steps of:
    (a) converting a medium containing a xylose source with a cell according to claim 7, which converts xylose to produce the metabolization product,
    (b) optionally obtaining the metabolization product,
    the metabolization product being selected from lactic acid, acetic acid, succinic acid, malic acid, 1-butanol, isobutanol, 2-butanol, other alcohols, amino acids, 1,3-propanediol, ethylene, glycerol, a β-lactam antibiotic or a cephalosporin, alkanes, terpenes, isoprenoids and the precursor molecule amorphadiene of the antimalarial drug artemisinin.

14. The method according to claim 13, wherein the medium contains a further carbon source.

15. The method according to claim 1, wherein the nucleic acid sequence that encodes a *Clostridium phytofermentans* xylose isomerase (XI) is at least 95% identical to the nucleic acid sequence SEQ ID NO:2.

16. A method for the recombinant expression and production of a functional xylose isomerase or for the conversion of xylose to xylulose by an isolated host cell, wherein said isolated host cell is a yeast cell selected from the group consisting of *Saccharomyces cerevisiae, Saccharomyces bulderi, Saccharomyces barnetti, Saccharomyces exiguus, Saccharomyces uvarum, Saccharomyces diastaticus, Kluyveromyces lactis, Kluyveromyces marxianus,* and *Kluyveromyces fragilis,* wherein said method comprises:
    (a) isolating the host cell and transforming the host cell with a nucleic acid expression construct comprising:

(i) a nucleic acid sequence encoding a *Clostridium phytofermentans* xylose isomerase (XI), having an amino acid sequence that is at least 95% identical to the amino acid sequence SEQ ID NO: 1, and (ii) a promoter operatively linked with the nucleic acid sequence, allowing for the expression of the *Clostridium phytofermentans* xylose isomerase (XI) in the cell, (b) expressing the nucleic acid encoding the *Clostridium phytofermentans* xylose isomerase, which imparts to the host cell the capability to isomerize xylose into xylulose.

17. An isolated host cell, wherein said host cell is a yeast cell selected from the group consisting of *Saccharomyces cerevisiae, Saccharomyces bulderi, Saccharomyces barnetti, Saccharomyces exiguus, Saccharomyces uvarum, Saccharomyces diustaticus, Kluyveromyces lactis, Kluyveromyces marxianus*, and *Kluyveromyces fragilis* and said host cell is transformed with a nucleic acid expression construct comprising:

(a) a nucleic acid sequence encoding a *Clostridium phytofermentans* xylose isomerase (XI), having an amino acid sequence that is at least 95% identical to the amino acid sequence SEQ ID NO: 1, and (b) a promoter operatively linked with the nucleic acid sequence, allowing for the expression of the *Clostridium phytofermentans* xylose isomerase (XI) in the cell, wherein the expression of the nucleic acid expression construct produces a functional xylose isomerase in the host cell and imparts to the host cell the capability to isomerize xylose into xylulose.

18. The isolated host cell according to claim 5, wherein:

the *Clostridium phytofermentans* xylose isomerase (XI) has the sequence of SEQ ID NO: 1, or the nucleic acid encoding the *Clostridium phytofermentans* xylose isomerase (XI) has the sequence of SEQ ID NO: 2.

19. The method according to claim 1, wherein the yeast cell is *Saccharomyces cerevisiae*.

20. The isolated host cell according to claim 5, wherein the yeast cell is *Saccharomyces cerevisiae*.

* * * * *